(12) United States Patent
Nemirovsky

(10) Patent No.: US 10,598,557 B2
(45) Date of Patent: Mar. 24, 2020

(54) PRESSURE LEVEL SENSING DEVICE AND A METHOD FOR SENSING PRESSURE

(71) Applicants: Todos Technologies Ltd., Airport City (IL); TECHNION RESEARCH AND DEVELOPMENT FOUNDATION LTD., Haifa (IL)

(72) Inventor: Yael Nemirovsky, Haifa (IL)

(73) Assignee: Todos Technologies Ltd., Airport City, IL (US)

( * ) Notice: Subject to any disclaimer, the term of this patent is extended or adjusted under 35 U.S.C. 154(b) by 137 days.

(21) Appl. No.: 15/743,678

(22) PCT Filed: Jul. 12, 2016

(86) PCT No.: PCT/IL2016/050745
§ 371 (c)(1),
(2) Date: Jan. 11, 2018

(87) PCT Pub. No.: WO2017/009827
PCT Pub. Date: Jan. 19, 2017

(65) Prior Publication Data
US 2018/0202884 A1   Jul. 19, 2018

Related U.S. Application Data

(60) Provisional application No. 62/191,433, filed on Jul. 12, 2015.

(51) Int. Cl.
  *G01L 11/00*  (2006.01)
  *G01L 21/12*  (2006.01)
  *G01N 27/407*  (2006.01)

(52) U.S. Cl.
  CPC ............ *G01L 11/002* (2013.01); *G01L 21/12* (2013.01); *G01N 27/4077* (2013.01)

(58) Field of Classification Search
  CPC ......... G01L 11/002; G01L 21/12; G01L 9/02; G01N 27/4077
  USPC .......................................................... 73/754
  See application file for complete search history.

(56) References Cited

U.S. PATENT DOCUMENTS

| | | | |
|---|---|---|---|
| 8,171,801 B2 * | 5/2012 | Le Noc | G01L 21/14 73/754 |
| 9,022,644 B1 * | 5/2015 | Arft | G01K 7/226 374/116 |
| 9,677,948 B1 * | 6/2017 | Arft | G01K 7/226 |

* cited by examiner

*Primary Examiner* — Octavia Hollington
(74) *Attorney, Agent, or Firm* — Reches patents

(57) ABSTRACT

A pressure sensing device that includes a pressure sensing element that is of microscopic scale and has a pressure level dependent thermal parameter; a signal source that is configured to supply an input electrical signal to the pressure sensing element; and a monitor that is configured to (a) measure electrical output signals generated by the pressure sensing element as a result of the supply of the input electrical signal and (b) estimate a pressure level applied on the pressure sensing element based on the electrical output signals.

19 Claims, 25 Drawing Sheets

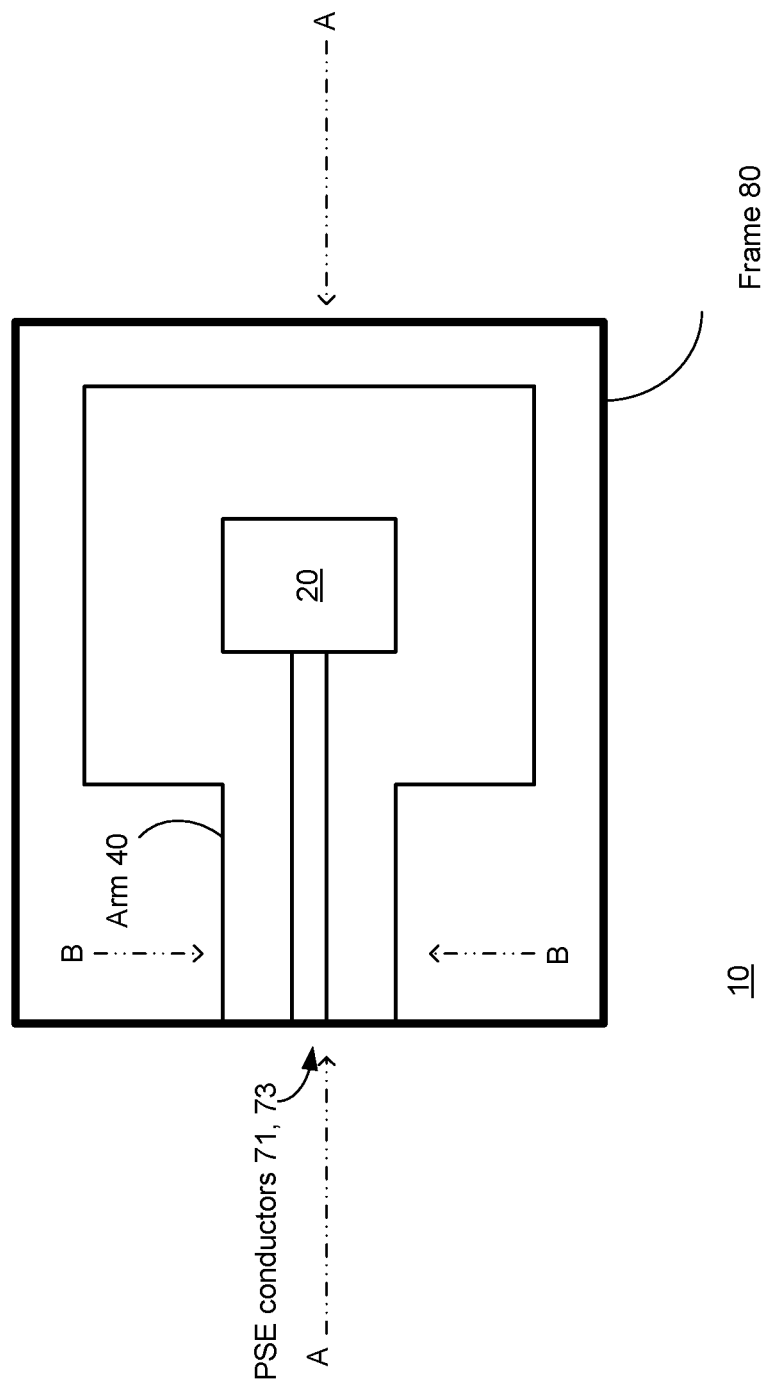

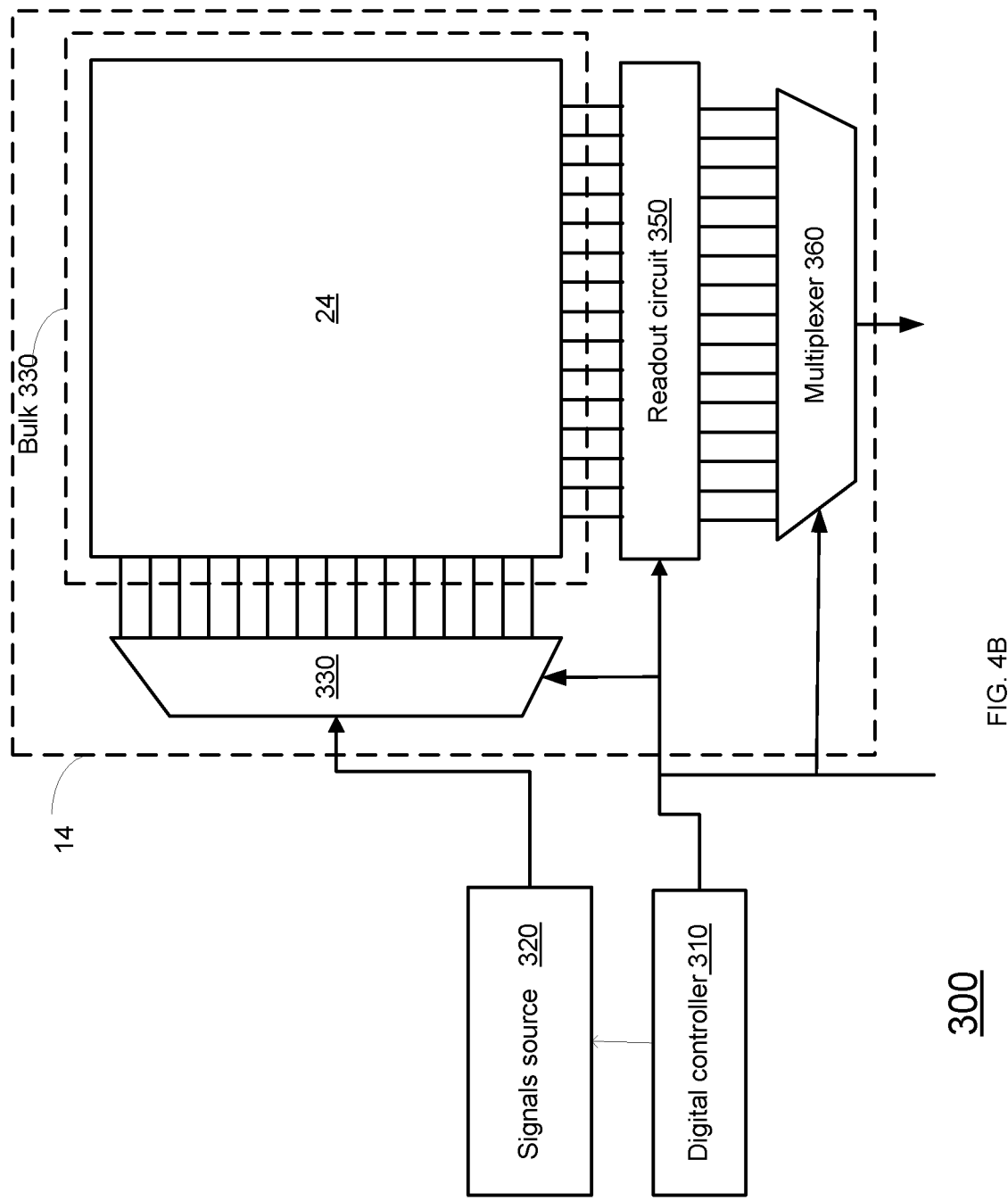

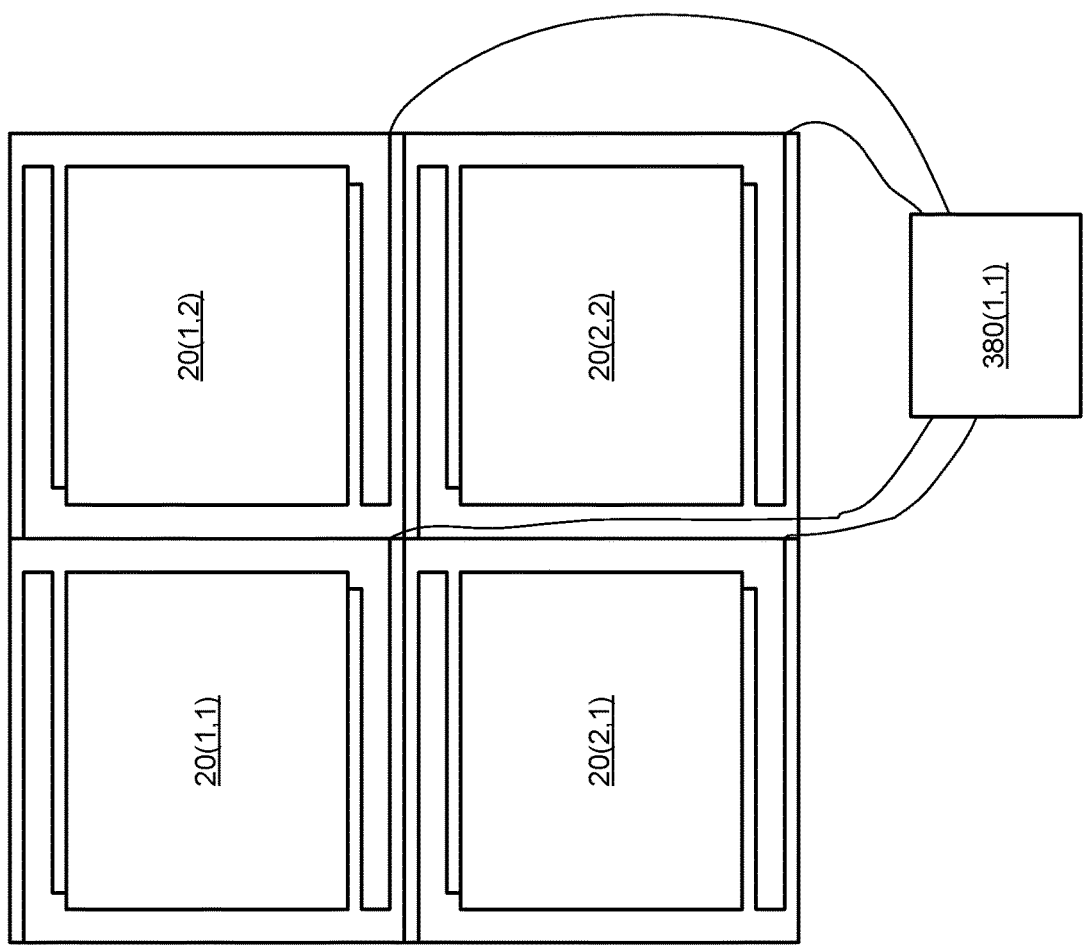

US 10,598,557 B2

PRESSURE LEVEL SENSING DEVICE AND A METHOD FOR SENSING PRESSURE

CROSS REFERENCE TO RELATED APPLICATIONS

This application claims priority from US provisional patent filing date Jul. 12, 2015, Ser. No. 62/191,433 which is incorporated herein by reference.

BACKGROUND OF THE INVENTION

Wikipedia defines Wafer level packaging (WLP) as the technology of packaging an integrated circuit while still part of the wafer, in contrast to the more conventional method of slicing the wafer into individual circuits (dice) and then packaging them. WLP is essentially a true chip-scale package (CSP) technology, since the resulting package is practically of the same size as the die. Wafer-level packaging allows packaging, test, and burn-in at wafer level at the fab in order to streamline the manufacturing process undergone by a device from silicon start to customer shipment of packaged system.

Wafer-level packaging includes extending the wafer fab processes to include device interconnection and device protection processes. Most other kinds of packaging do wafer dicing first, and then put the individual die in a plastic package and attach the solder bumps. Wafer-level packaging involves attaching the top and bottom outer layers of packaging, and the solder bumps, to integrated circuits while still in the wafer, and then wafer dicing.

It has been found that very low pressure levels should be maintained within a WLP wafer for a wide range of MEMS devices.

There is a growing need to provide a reliable manner of measuring the pressure level within the MEMS systems that are implemented on a WLP wafer. Especially for measuring the pressure levels at one or more points in time after the WLP package has been diced and elements of the WLP outgas thereby increase the pressure level within the MEMS systems.

SUMMARY

A method, semiconductor device and a pressure sensing device as illustrated in the specification and the claims.

According to an embodiment of the invention there may be provided a pressure sensing device may include a pressure sensing element that may be of microscopic scale (has one or more dimensions that of a magnitude of less than one hundred micron, of about a micron, a sub-micron, a nanometer or sub-nanometer scale) and has a pressure level dependent thermal parameter; a signal source that may be configured to supply an input electrical signal to the pressure sensing element; and a monitor that may be configured to (a) measure electrical output signals generated by the pressure sensing element as a result of the supply of the input electrical signal and (b) estimate a pressure level applied on the pressure sensing element based on the electrical output signals.

The pressure sensing element may be positioned within a chamber and wherein the pressure level applied on the pressure sensing element is a pressure level within the chamber.

The pressure sensing element may be used solely for sensing pressure.

The pressure sensing element may not be solely dedicated for sensing pressure. Thus, the pressure sensing element may be used as a pressure sensing element during some points of time and may be used for another purpose (any function that differs from pressure sensing) at other points in time.

The pressure level dependent parameter may be a thermal time constant of the pressure sensing element.

The monitor may be configured to estimate the thermal time constant of the pressure sensing element based on a steady state electrical output signal and based on an initial rate of change of the electrical output signals.

The input electrical signal may include spaced apart pulses.

The pressure sensing element may be a Microelectromechanical Systems (MEMS) element or a Nanoelectromechanical Systems (NEMS) element.

The pressure sensing element may be a suspended transistor that may be thermally isolated from a bulk of the pressure sensing device.

The pressure sensing device may be manufactured by wafer level packaging technology.

According to an embodiment of the invention there may be provided a method for sensing a pressure level applied on a pressure sensing element, the method may include supplying an input electrical signal to the pressure sensing element; wherein the pressure sensing element may be of microscopic scale and has a pressure level dependent thermal parameter; measuring electrical output signals generated by the pressure sensing element as a result of the supply of the input electrical signal; and estimating a pressure level applied on the pressure sensing element based on the electrical output signals.

The pressure sensing element may be positioned within a chamber and wherein the pressure level applied on the pressure sensing element may be a pressure level within the chamber.

The method may include utilizing the pressure sensing element only for sensing pressure.

The method may include utilizing the pressure sensing element for operations that differ from sensing pressure.

The pressure level dependent parameter may be a thermal time constant of the pressure sensing element.

The method may include estimating the thermal time constant of the pressure sensing element based on a steady state electrical output signal and based on an initial rate of change of the electrical output signals.

The input electrical signal may include spaced apart pulses.

The pressure sensing element may be a Microelectromechanical Systems (MEMS) element or a Nanoelectromechanical Systems (NEMS) element.

The pressure sensing element may be a suspended transistor that may be thermally isolated from a bulk of the pressure sensing device.

The pressure sensing device may be manufactured by wafer level packaging technology.

According to an embodiment of the invention there may be provided a semiconductor device that may include an enclosure and a semiconductor apparatus that may be enclosed in the enclosure; wherein the semiconductor apparatus may include a pressure sensing element that may be of microscopic scale and has a pressure level dependent thermal parameter; a signal source that may be configured to supply, at different points in time, input electrical signals to the pressure sensing element; and a monitor that may be configured to (a) measure electrical output signals generated by the pressure sensing element as a result of the supply of the input electrical signals and (b) estimate a pressure level applied within the enclosure based on the electrical output signals. The pressure sensing apparatus may be a die, a wafer or any other semiconductor apparatus while the semiconductor device may be any mobile or stationary device such as an alarm system, a computer, and the like. The term semiconductor device (the same applied to the semiconductor apparatus) means that the device has some semiconductor elements.

The semiconductor apparatus may be manufactured by wafer level packaging.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1B illustrates a frame, an arm, a pressure sensing element and various conductors according to an embodiment of the invention;

FIG. 4B illustrates a pressure sensing device according to an embodiment of the invention;

FIG. 5A illustrates various semiconductor pressure sensors and an interface according to an embodiment of the invention;

Figure 1A:
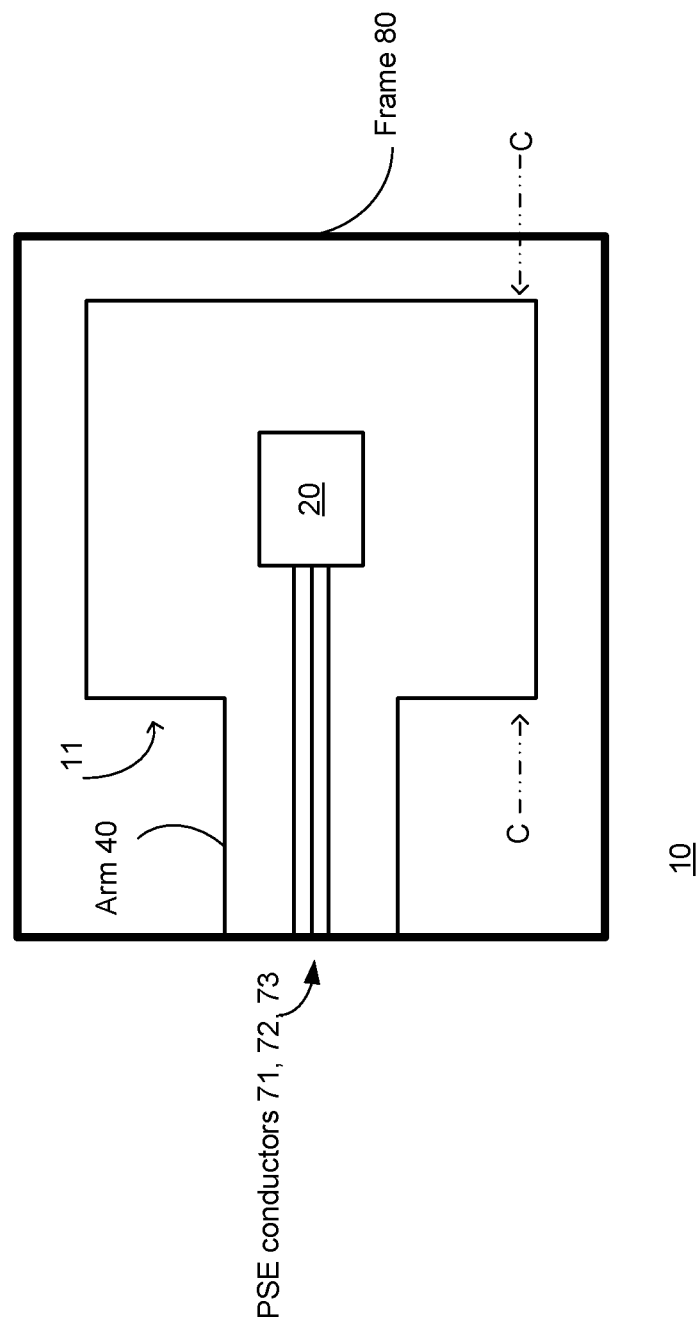
FIG. 1A illustrates a frame, an arm, a pressure sensing element and various conductors according to an embodiment of the invention.

It will be appreciated that for simplicity and clarity of illustration, elements shown in the Figures have not necessarily been drawn to scale. For example, the dimensions of some of the elements may be exaggerated relative to other elements for clarity. Further, where considered appropriate, reference numerals may be repeated among the Figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a pressure sensing device capable of executing the method.

Any reference in the specification to a pressure sensing device should be applied mutatis mutandis to a method that may be executed by the pressure sensing device.

There is provided a pressure sensing element that may be included in a WLP wafer. The following figures illustrate some example of a pressure sensing element. The pressure sensing element may include a transistor, a diode, and the like.

A pressure sensing element of microscopic scale (for example having micron scale, sub-micron scale and even nanometric scale dimensions) has a pressure level dependent thermal parameter. The pressure level dependent thermal parameter may be a thermal time constant. The pressure sensing element may be fed by input signals (also referred to as bias signals) that cause the pressure sensing element to heat. Detection signals (also referred to as output signals or detection signals) from the pressure sensing element are measured to provide information about the heating process of the pressure sensing element. The detection signals are processed to determine pressure level applied on the pressure sensing element.

The pressure sensing element (PSE) is small and can be easily fit within small system on chip and small circuits.

The pressure sensing element may be solely dedicated to pressure measurement but may be used for other purposes. For example, when not used as a pressure sensing element that pressure sensing element may be used for sensing radiation (Terahertz, infrared, visible light or any other radiation) or for any other purpose. Namely, a MEMS device that can detect any physical or chemical parameter of interest and importance.

A semiconductor die may include one or more pressure sensing elements.

There may be provided a semiconductor device (for example a stack of wafers of a die and top and bottom covers) that includes an enclosure (can include, for example, top and bottom wafers or top and bottom covers) and a semiconductor apparatus (an intermediate wafer or an intermediate die) that is enclosed in the enclosure; wherein the semiconductor apparatus may include a pressure sensing element that is of microscopic scale and has a pressure level dependent thermal parameter; a signal source that is configured to supply an input electrical signal to the pressure sensing element; and a monitor that is configured to (a) measure electrical output signals generated by the pressure sensing element as a result of the supply of the input electrical signal and (b) estimate a pressure level applied within the enclosure based on the electrical output signals.

According to an embodiment of the invention the monitor is not included in the semiconductors device.

FIG. 1A illustrates a frame 80, an arm 40, a pressure sensing element 11 and various conductors according to an embodiment of the invention.

The pressure sensing element is also denoted PSE.

Arm 40 is connected between frame 80 to suspended element 11 that includes pressure sensing element 20 and PSE conductors 71, 72 and 73.

PSE conductors 71, 72 and 73 may be coupled to three ports of the pressure sensing element 20 (for example source, drain and gate or emitter, collector and base).

PSE conductors 71, 72 and 73 can be made of a material that such as polysilicon that has a low thermal conductivity but has a good electrical conductivity.

A readout circuit (not shown) is configured to heat the pressure sensing element 20 by providing a predefined electrical signal (such as but not limited to a current pulse and/or a voltage pulse) that heats the pressure sensing element 20 by Joule heating.

The reaction of the pressure sensing element 20 to the predefined electrical signal is measured (for example by the readout circuit) and the thermal time constant of the pressure sensing element 20 is found.

The thermal time constant is translated to a pressure level of the surroundings of the pressure sensing element 20. The translation can be made by using a look up table, an equation, by a training process that involves applying different pressure levels and measuring the thermal time constant, and the like.

FIG. 1B illustrates a frame 80, an arm 40, a pressure sensing element (PSE) 11 and various conductors according to an embodiment of the invention.

In FIG. 1B there are two PSE conductors 71 and 73 and not three conductors. The number of conductors may exceed three.

Figure 2:
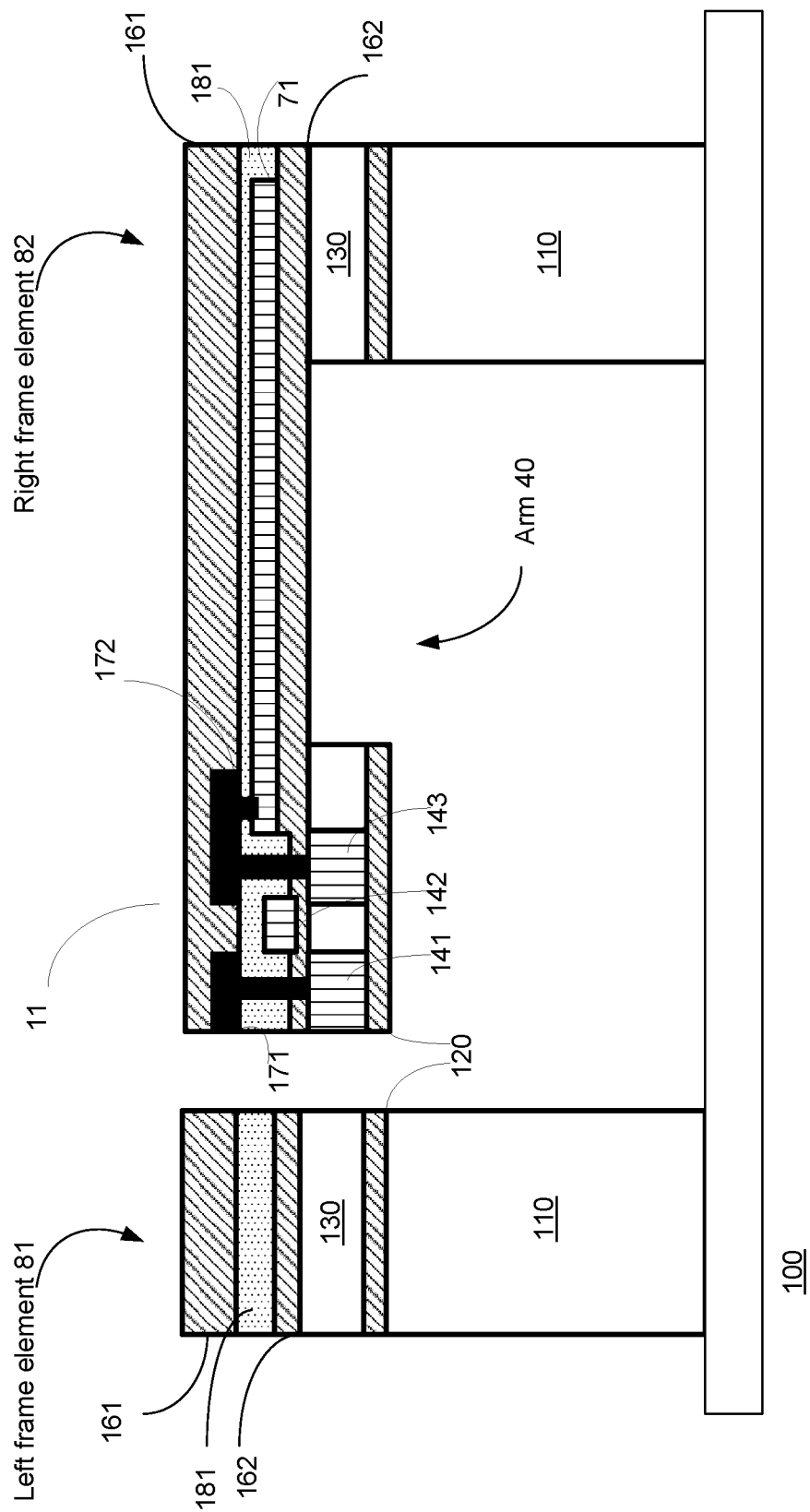
FIG. 2 is a cross sectional view of a frame, an arm and a pressure sensing element according an embodiment of the invention.

FIG. 1A illustrates an imaginary plane C-C. FIG. 2B illustrates a cross section along plane C-C.

In FIG. 1B the pressure sensing element 20 can be a CMOS diode or any other diode as well as a transistor that is coupled as a diode.

FIG. 1B illustrates imaginary planes A-A and B-B. FIG. 2A illustrates a cross section along plane A-A. FIG. 2B illustrates a cross section along plane B-B.

Figure 1C:
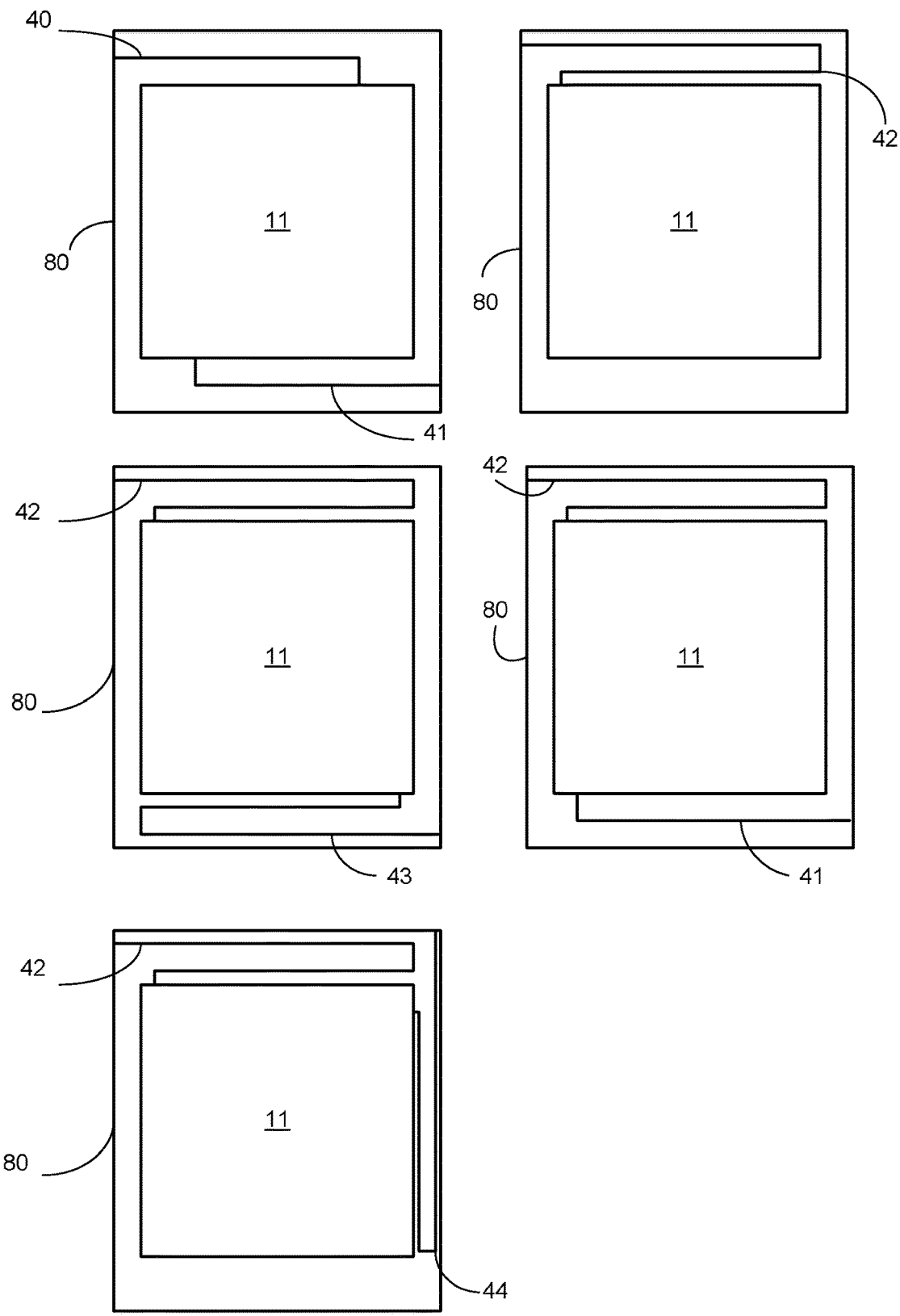
FIG. 1C illustrates a frame, various arms, and various semiconductor pressure sensing elements according to various embodiments of the invention.

FIG. 1C illustrates a frame 80, various arms 40, 41, 42, 43 and 44 and various semiconductor pressure sensing elements 11 according to various embodiments of the invention.

FIG. 1C illustrates that a pressure sensing element 11 may be supported by one arm or more arms (for example two arms), and that the arms may have different shapes.

The shape and size of the arms may change. As a rule of thumb longer arms (for example arms 42, 43 and 44) provide better thermal isolation from shorter arms (for example arms 40 and 41) that are made of the same materials.

FIG. 2A is a cross sectional view (along plane A-A) of a frame, an arm and a pressure sensing element according an embodiment of the invention.

Frame 80 is illustrated as has having a left frame element 81 and a right frame element 82.

FIG. 2A illustrates a semiconductor temperature sensing element such as a CMOS transistor that includes drain 141, source 143 and gate 142. Drain 141 is coupled to a drain conductor 171. Source 143 is coupled to a source conductor 172. Source conductor 172 and drain conductor 171 are made of metal or polysilicon or active silicon and may be coupled to PSE conductors 71 and 72 respectively. The gate 142 may be coupled to a gate conductor (not shown).

Drain 141 and source 143 may be positioned above a thin silicon dioxide layer 120 that can be formed on top of thick silicon bulk 110.

Bulk 110 and device layer 130 may be micro-machined or nano-machined to form a suspended semiconductor pressure sensing element.

Thin silicon dioxide layer 120 of the buried oxide may serve as an etch stop layer for the bulk micromachining process and separates the bulk silicon from the thin device single crystal silicon layer 130.

The stack of thin device silicon layer 130 on top of thin silicon dioxide layer 120 on top of thick silicon bulk 110 is known as SOI and may be fabricated by several techniques, well known for the experts. An increase in the top silicon layer thickness, and increased control of its properties, is preferably achieved using epitaxial growth of silicon.

The non-etched silicon bulk 110 serves as a heat sink to the thermal sensors due to the high thermal conductivity of the silicon and the large thickness of silicon bulk 110. Silicon bulk 110 is etched under the sensor area in order to provide thermal isolation for increased temperature responsivity.

Above the etched area a structure composed of layers such as but not limited to Complementary Metal Oxide Semiconductor (CMOS) thin film layers—such as first insulating layers 161 and second insulating layer 162—both known as Inter Level Dielectrics.

FIG. 2A illustrates first and second insulating layers 161 and 162 as being separated by intermediate layer 181.

Figure 3A:
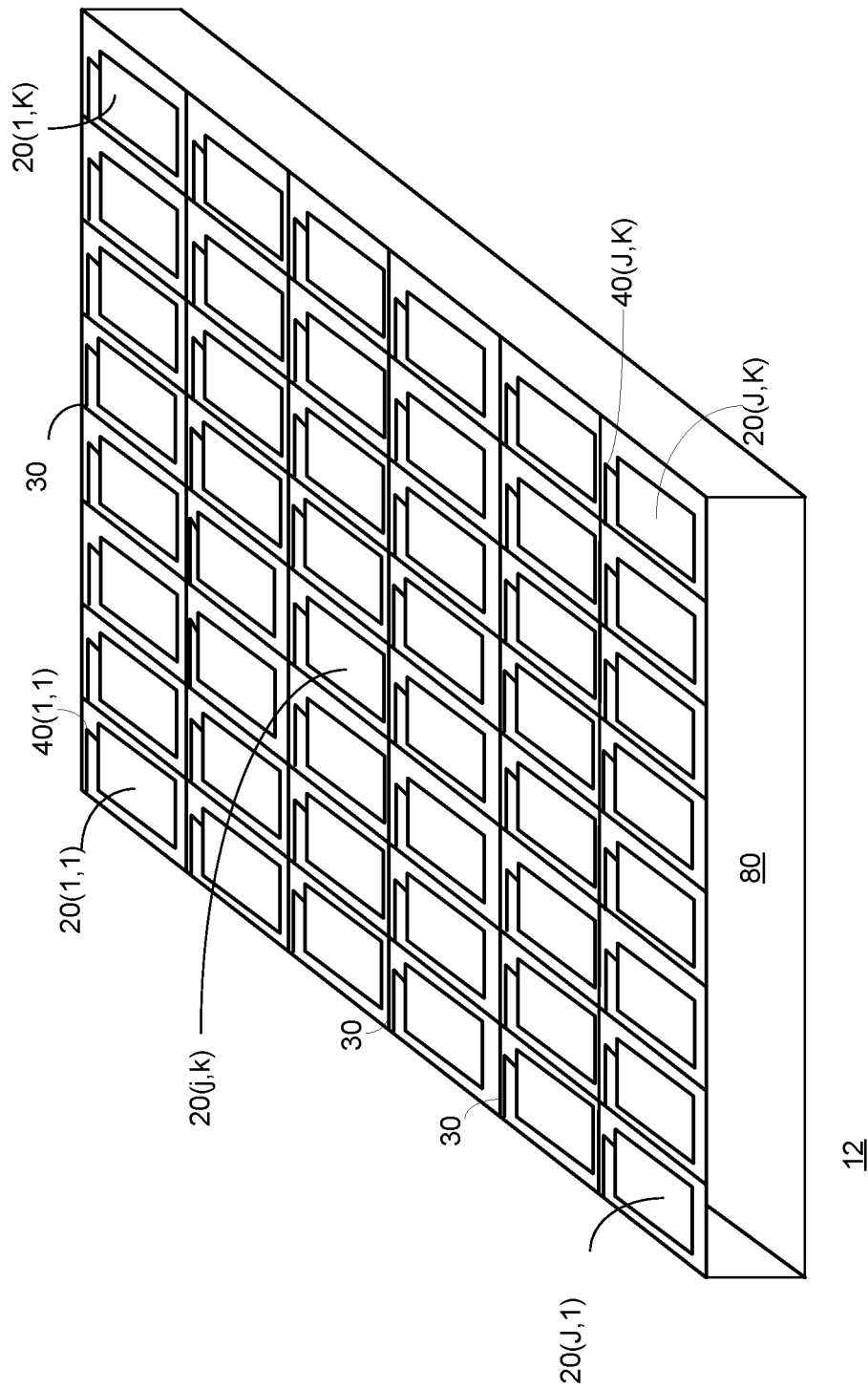
FIG. 3A illustrates frame, arms and an array of semiconductor elements according to an embodiment of the invention.

FIG. 3A illustrates an array of semiconductor elements, according to various embodiments of the invention.

One, some or all of the semiconductor elements may be pressure sensor elements. Using more semiconductor elements of the array as pressure sensors may increase the accuracy of the pressure measurement. As a rule of thumb, using N semiconductor elements as pressure sensing element increases the signal to noise ration by a square root of N.

A semiconductor element that is used as a pressure sensor element may be dedicated for pressure level measurements but may have other purposes. For example—the array may be a thermal, infrared, Terahertz, visible light sensor array.

FIG. 3A illustrates a rectangular array of semiconductor elements 20(1,1)-20(J,K) that include K columns and J rows of semiconductor elements. J and K are positive integers that exceed one.

The semiconductor elements of the array are supported by arms 40(1,1)-40(J,K) to a grid of frames collectively denoted 80.

Each semiconductor element may be connected to one or more arms.

Figure 3B:
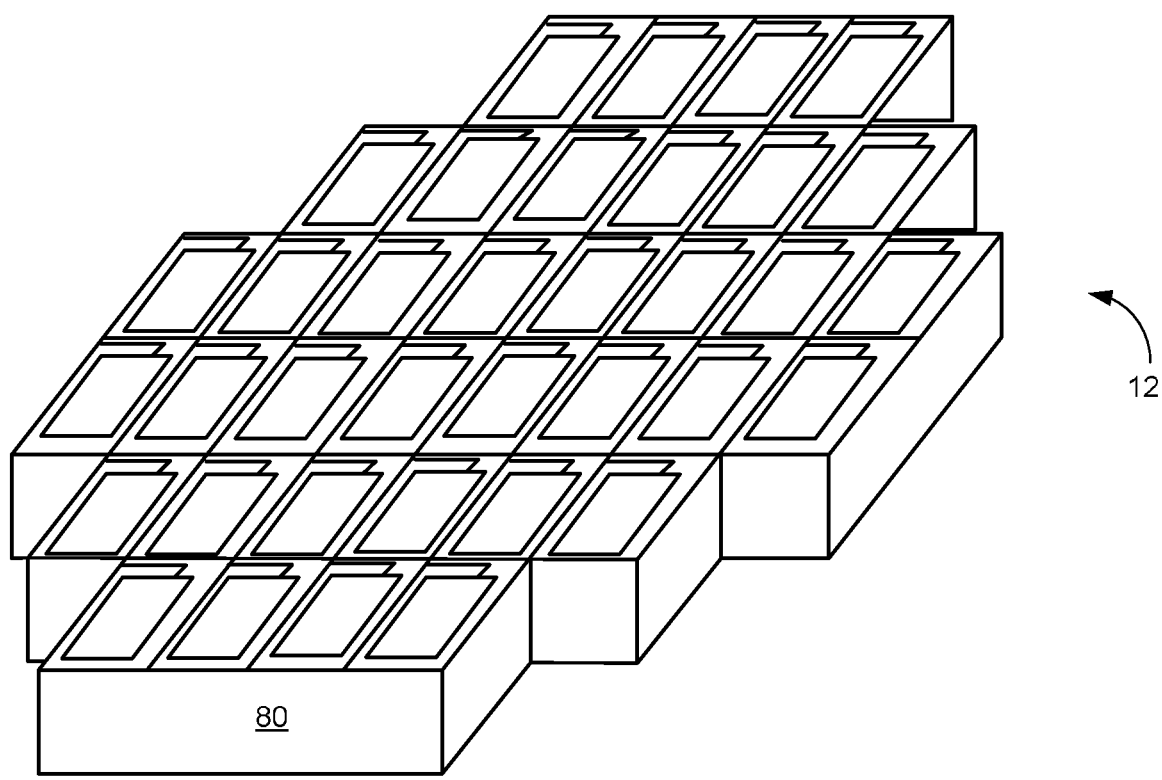
FIG. 3B illustrates frames, arms and an array of semiconductor elements according to an embodiment of the invention.

The semiconductor elements may be arranged to form other arrays. For example—a linear array, a non-rectangular array, a polygonal array, a circular array or any arrangements of multiple sensing elements. FIG. 3B illustrates a non-rectangular array of semiconductor elements.

Figure 4A:
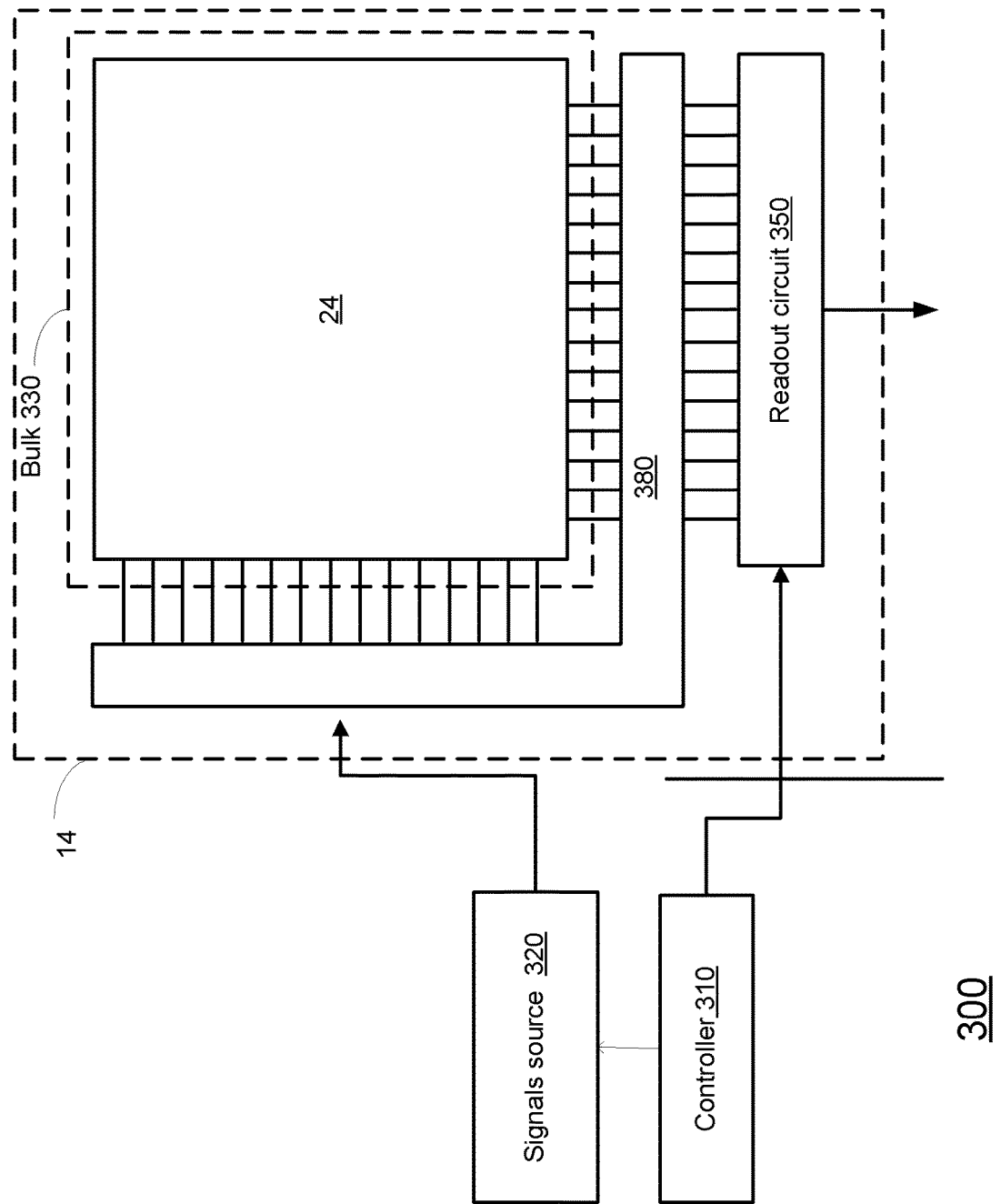
FIG. 4A illustrates a pressure sensing device according to an embodiment of the invention.

FIG. 4A illustrates a pressure sensing device 300 according to an embodiment of the invention.

Pressure sensing device 300 includes a controller 310, signals source 320, bulk 330, interfacing module 380, readout circuit 350 and an array 24 of semiconductor elements—at least one of which may operate as a pressure sensing element.

Although interfacing module 380 is illustrates as a separate entity from the array 24, both array 24 and interfacing module 380 may be integrated and may form a part of the WLP wafer.

Interfacing module 380 may couple between the array 24 to the signals source 320 and to the readout circuit 350.

Readout circuit 350 may read detection signals from one or more semiconductor elements at a time. For example—the readout circuit 350 may read a single row of array 24, a part of a row, more than a single row, a column, a part of a column, more than a column and even the entire array at once.

Readout circuit 350 may read current detection signals, voltage detection signals, differential detection signals and the like.

Readout circuit 350 may send predefined electrical signals (input signals, bias signals) for heating one or more semiconductor pressure sensing elements, may measure the response (signals outputted from) the one or more semiconductor pressure sensing elements and may either process the response to determine the pressure levels at the vicinities of the one or more semiconductor pressure sensing elements or may send the measurements to another device (not shown) that will determine the pressure levels at the vicinities of the one or more semiconductor pressure sensing elements.

According to an embodiment of the invention the interfacing module 380 may also electrically couple between different semiconductor elements of the array 24. The interfacing module 380 may couple certain semiconductor elements of the array in serial to each other during one measurement and couple the certain semiconductor elements of the array in parallel to each other during another measurement. Any combination of serial and parallel couplings between semiconductor elements may be provided. The interfacing module 380 may include any combination of switches, interconnects and the like.

Signals source 310 is configured to supply bias signals (input signals) to at least one pressure sensing element of the array 24. The bias signals may include voltage bias signals and/or current bias signals.

The bias signals may be provided in a continuous manner or in a non-continuous manner. The latter may reduce the power consumption of the pressure sensing device.

Controller 310 is configured to control the operation of the pressure sensing device 300.

Controller 310, signals source 320, bulk 330, interfacing module 380, readout circuit 350 and array 24 of semiconductor pressure sensing elements may be formed on the same chip. The pressure sensing device 300 may be fabricated using CMOS technology.

FIG. 4B illustrates a pressure sensing device 300 according to an embodiment of the invention.

In FIG. 4B the interfacing module 380 is illustrates as including (i) a de-multiplexer 330 that is coupled between signals source 320 and array 24, and (ii) a multiplexer 360 that is coupled between readout circuit 350 and an output port of pressure sensing device.

FIG. 5A illustrates pressure sensing elements 20(1,1), 20(1,2), 20(2,1) and 20(2,2) and a part 380(1,1) of an interfacing module according to an embodiment of the invention.

Part 380(1,1) may provide bias signals (input signals) to each one of pressure sensing elements 20(1,1), 20(1,2), 20(2,1) and 20(2,2) and may receive and/or manipulate detection signals (output signals) from pressure sensing elements 20(1,1), 20(1,2), 20(2,1) and 20(2,2).

For example, part 380(1,1) may perform a manipulation by adding (or averaging) the detection signals from pressure sensing elements 20(1,1), 20(1,2), 20(2,1) and 20(2,2).

Figure 5B:
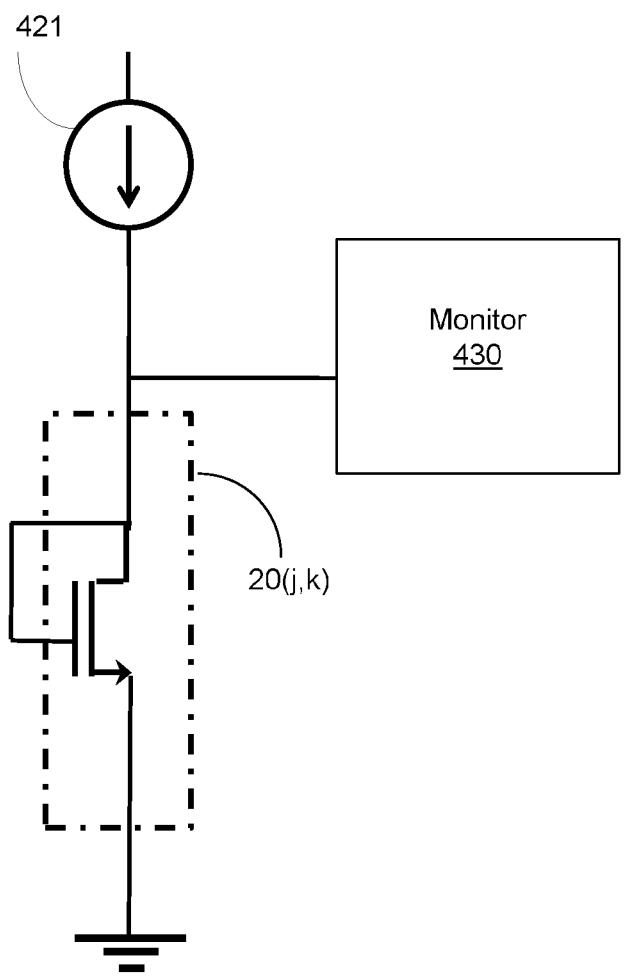
FIG. 5B illustrates a semiconductor pressure sensing element, a reference element, current sources and a voltage amplifier according to an embodiment of the invention.

FIG. 5B illustrates a pressure sensing element $20(j,k)$, a current source 421 and a monitor 430 according to an embodiment of the invention.

Pressure sensing element $20(j,k)$ may be a CMOS transistor that is coupled as a diode but may also be operated with 3 terminals A detection signal is outputted by pressure sensing element $20(j,k)$ and is a voltage detection signal. The detection signal reflects the temperature sensed by the semiconductor pressure sensing element.

The detection signal is fed to monitor 430 for measuring the change of voltage over time.

Current source 421 may belong to signals source 320 and may be provided, via interfacing module 380, to pressure sensing element $20(j,k)$.

Monitor 430 may belong to readout circuit 350 of FIGS. 4A and 4B.

Figure 5C:
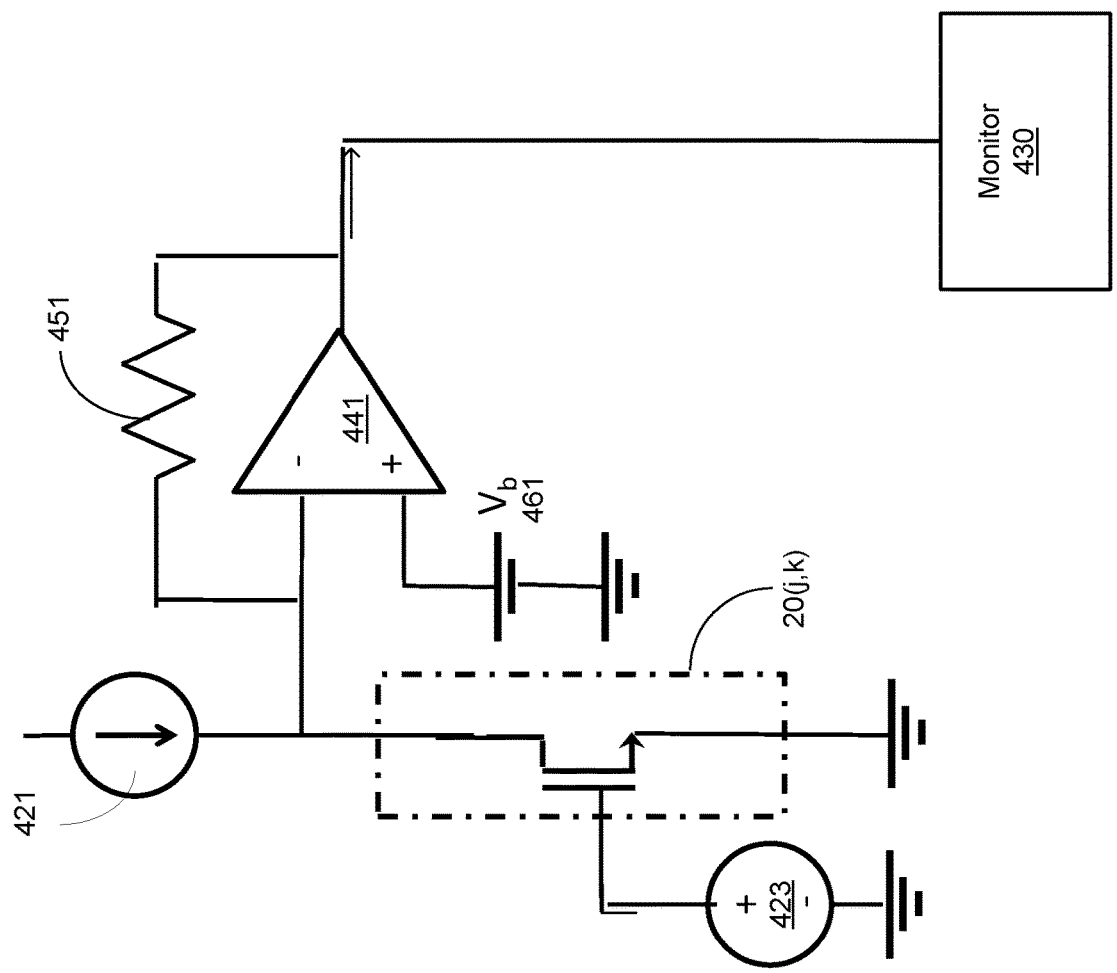
FIG. 5C illustrates a semiconductor pressure sensing element, a reference element, current sources, voltage sources, transimpedance amplifiers, a voltage amplifier and feedback resistors according to an embodiment of the invention.

FIG. 5C illustrates a pressure sensing element $20(j,k)$, current source 421, voltage sources 423 and 461, transimpedance amplifier 441, monitor 430 and feedback resistor 451 452 according to an embodiment of the invention.

In FIG. 5C the detection signal outputted by pressure sensing element $20(j,k)$ is a current detection signal.

Voltage source 423 provides a gate bias voltage to a gate of pressure sensing element $20(j,k)$.

A detection signal is outputted by pressure sensing element $20(j,k)$ and is a current detection signal. The detection signal reflects the temperature sensed by the semiconductor pressure sensing element.

First transimpedance amplifier 441 receives at its non-inverting input a bias voltage from voltage source 461.

A first current that is a difference between a first fixed current (from first current source 421) and the current detection signal is fed to an inverting input of first transimpedance amplifier 441 and to first feedback resistor 451 to provide a first intermediate voltage that is then fed to a non-inverting input of voltage amplifier 443.

Voltage amplifier 443 outputs an output signal that represents the difference between the reference signal and the detection signal—which indicates the temperature of the pressure sensing element 20(j,k).

Figure 6:
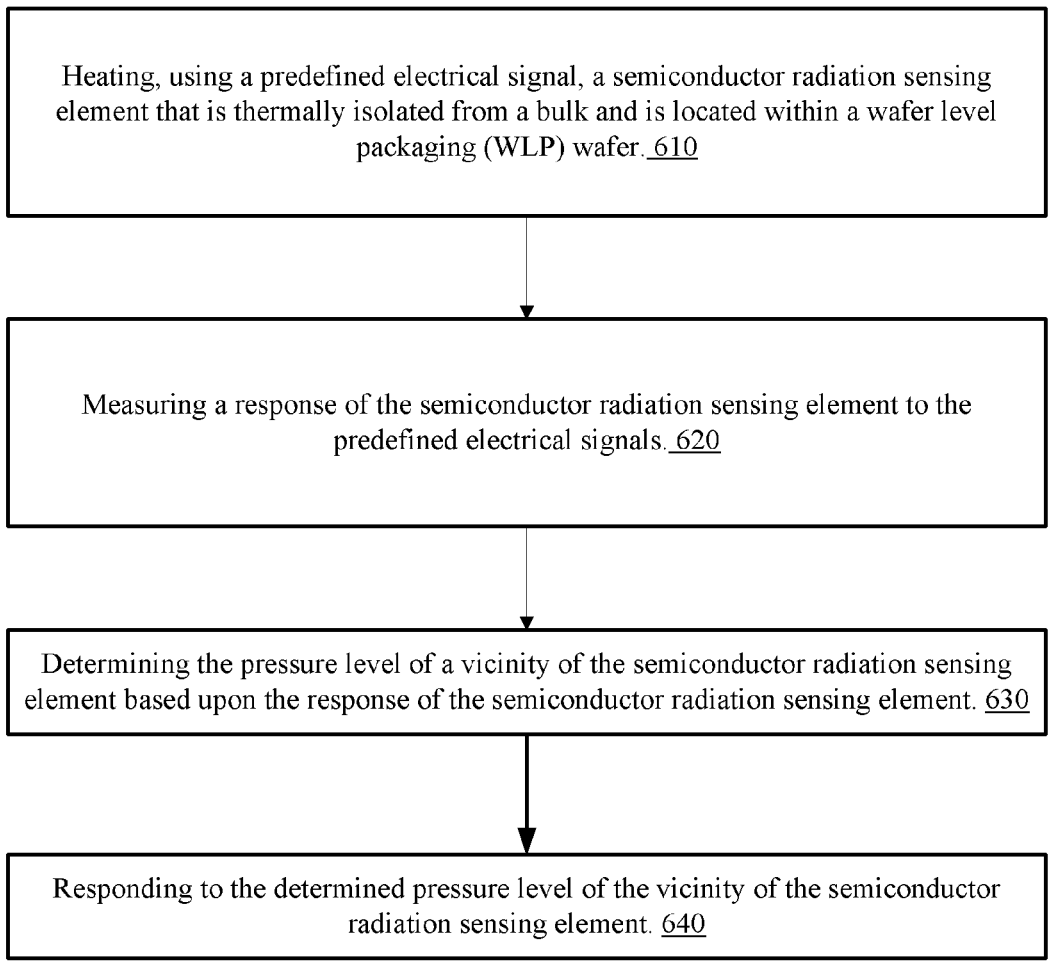
FIG. 6 illustrates a method according to an embodiment of the invention.

FIG. 6 illustrates method 600 according to an embodiment of the invention.

Method 600 may include step 610 of heating, using a predefined electrical signal, a semiconductor radiation sensing element that is thermally isolated from a bulk and is located within a wafer level packaging (WLP) wafer.

Step 610 may be followed by step 620 of measuring a response of the semiconductor radiation sensing element to the predefined electrical signals.

Step 620 may be followed by step 630 of determining the pressure level of a vicinity of the semiconductor radiation sensing element based upon the response of the semiconductor radiation sensing element.

Step 630 may be followed by step 640 of responding to the determined pressure level of the vicinity of the semiconductor radiation sensing element Method 600 may be executed by any of the pressure sensing devices illustrated in any of the drawings.

Figure 7:
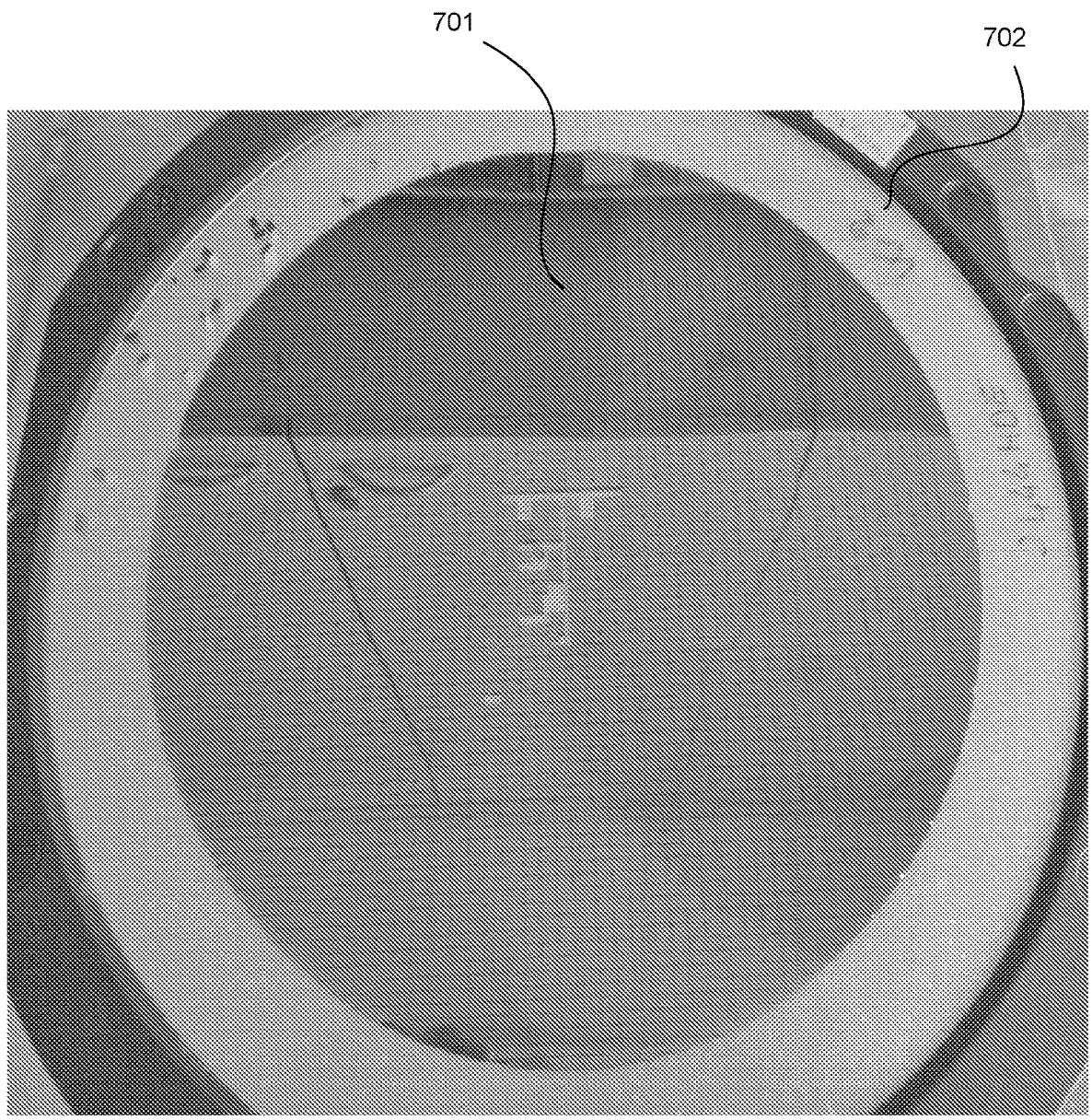
FIG. 7 illustrates a WLP wafer according to an embodiment of the invention.

FIG. 7 illustrates a WLP wafer 700 according to an embodiment of the invention. The WLP wafer include a bottom wafer (not shown) a semiconductor wafer that includes multiple dies 701 and a top wafer that includes a partially transparent frame 702.

Figure 8:
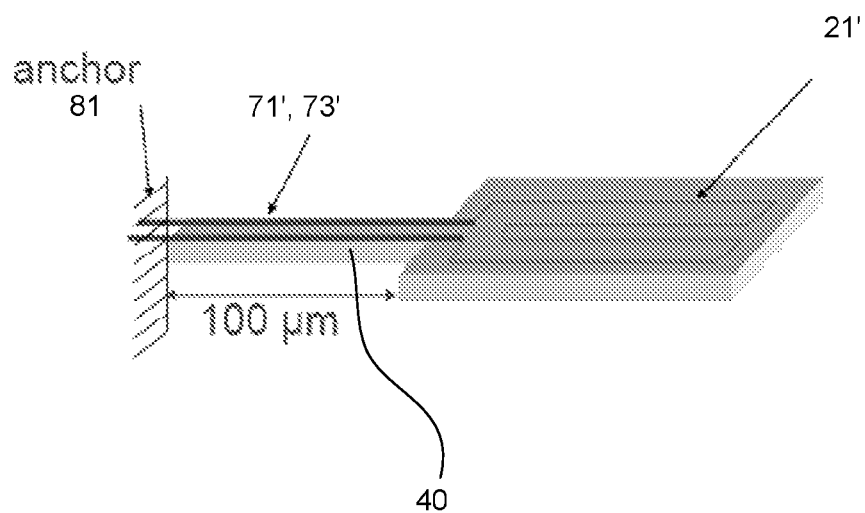
FIG. 8 illustrates a frame, an arm, a pressure sensing element and various conductors according to an embodiment of the invention.

FIG. 8 illustrates a frame (anchor 81), an arm that supports PSE conductors 71' and 73', and a pressure sensing element that includes a gate 21' according to an embodiment of the invention.

The PSE conductors 71' and 73' have a length of 100 Micron, are made of Aluminum (thermal conductivity of 200 W/K/m) and have a cross section of one square micron. The gate 21' is made of polysilicon and has a resistance of one thousand Ohms. The power of a current pulse that is provided to the pressure sensing element is 1 Mili-Ampere (mA).

Assuming a prefect vacuum the heat of pressure sensing element dissipates through the PSE conductors 71' and 73'.

The power provided to the pressure sensing element equals:

$$P_{gen} = I^2 R = (1\ mA)^2 * (1000\ Ohm) = 1\ mW.$$

The thermal conductivity G equals:

$$G = k*hw/L = 2*(200\ W/K/m)*(1\ micron)^2/(100\ Micron) = 4 \times 10^{-6}\ W/K.$$

$$\Delta T = P_{gen}/G = 250\ K.$$

Figure 9:
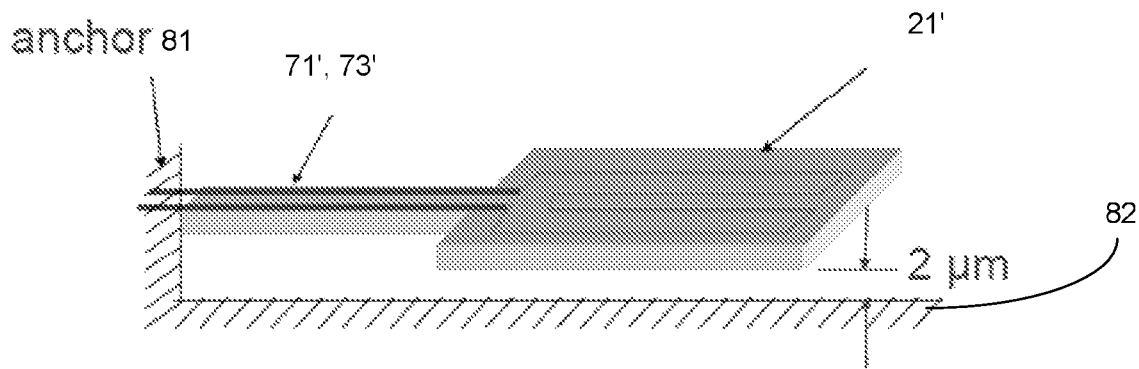
FIG. 9 illustrates a frame, an arm, a pressure sensing element and various conductors according to an embodiment of the invention.

FIG. 9 illustrates a frame (anchor 81), an arm that supports PSE conductors 71' and 73', and a pressure sensing element that includes a gate 21' according to an embodiment of the invention.

It is assumed that the vacuum is not ideal and that the heat of pressure sensing element dissipates through the air to the bulk 82. The distance between the pressure sensing element and the bulk is 2 microns. The pressure sensing element has a length of fifty microns and a width of is fifty microns. The thermal conductivity of the air is 0.026 W/K/m The thermal conductivity G equals:

$$G = k*hw/L = 2*(0.026\ W/K/m)*(50\ micron)^2/(2\ Micron) = 3.3 \times 10^{-5}\ W/K.$$

Figure 10:
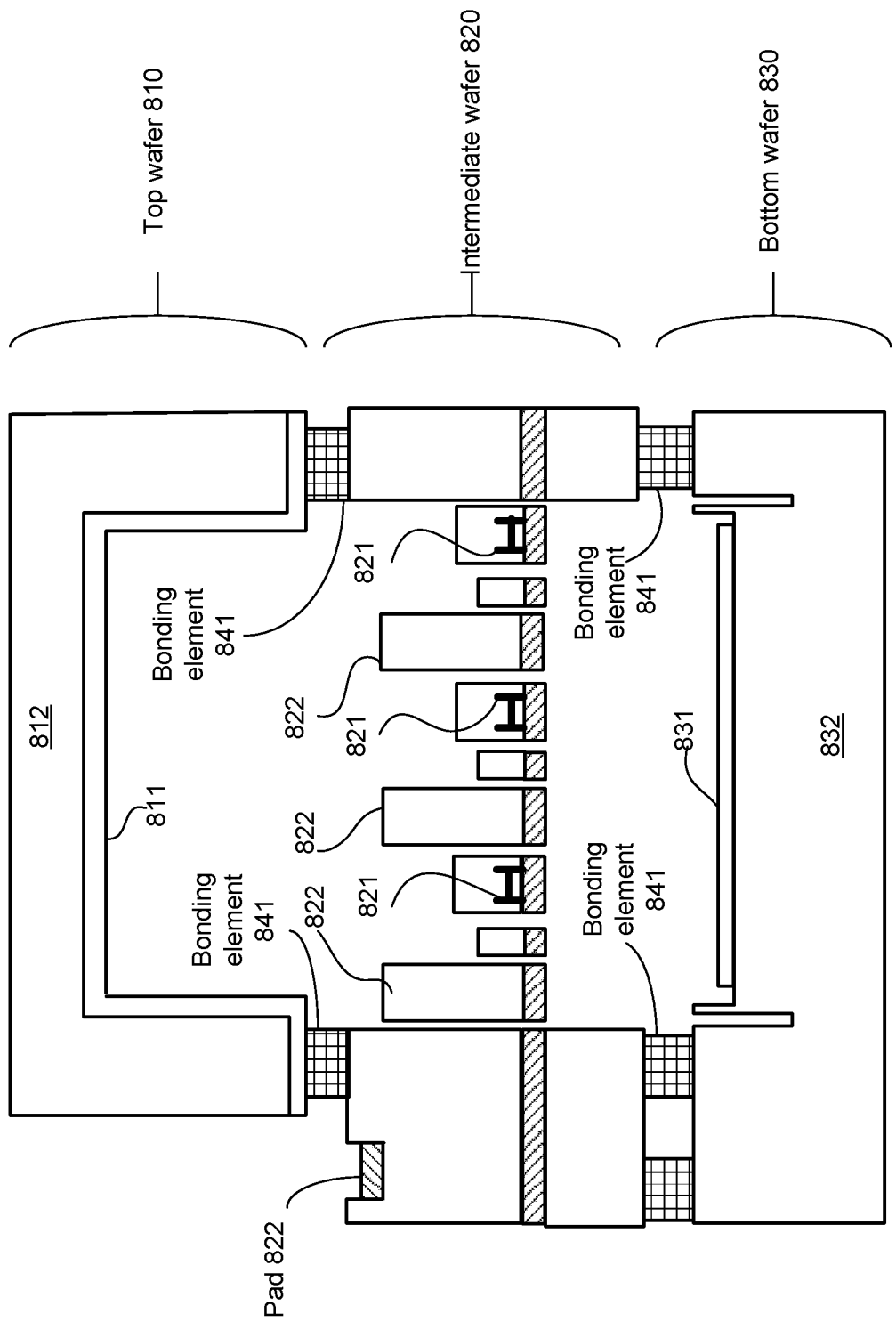
FIG. 10 is a cross sectional view of a WLP wafer that includes a top wafer an intermediate wafer and a bottom wafer according to an embodiment of the invention.

FIG. 10 is a cross sectional view of a WLP wafer that includes a top wafer 810, an intermediate wafer 820 and a bottom wafer 830 according to an embodiment of the invention.

The intermediate wafer 820 includes one or more pressure sensing elements 821 and parts of frames and/or arms 822. The intermediate wafer 820 includes multiple apertures and in order to provide a closed chamber the intermediate wafer 820 has to be surrounded (both on top and on bottom) by top wafer 810 and bottom wafer 830.

In FIG. 10 the bottom wafer 830 serves as an optical window with a filter (lambda half cavity-remove) and includes a bulk 831 and reflecting element 831.

In FIG. 10 the top wafer 810 includes bulk 811 and oxide 822 for preventing a formation of a ghost image.

FIG. 10 illustrated bonding elements such as 841 between the wafers and also shows pads 833 for supplying input signals and receiving output signals.

It should be noted that the pressure sensing element may be manufacturing by wafer level packaging or by any other manufacturing process (including a manufacturing process in which the dies are diced before packaging the die.

Test Results

These test results were obtained by measuring pressure levels sensed by pressure sensing elements of different wafers. These test results were measured using direct differential measurements of pressure sensing elements that are thermal MOS transistors (TMOS) manufactured by STMicroelectronics of a WLP wafer stack packaged by double glass-frit.

The thermal time constant was measured by heating the pressure sensing elements with Joule power and monitoring the dependence of the measured voltage upon time.

Temperature of TMOS is changing exponentially with time in case of constant Joule heat:

$$\Delta T(t) = \frac{P}{G_{th}} \cdot (1 - e^{-\frac{t}{\tau}}),$$

Where P—Joule heat power, $G_{th}$—thermal conductivity, T—temperature, t—time, τ—thermal time constant.

Differential voltage ΔV has exponential time dependence:

$$\Delta V(t) = \frac{dV}{dT} \cdot \Delta T(t) = \frac{dV}{dT} \cdot \frac{P}{G_{th}} \cdot (1 - e^{-\frac{t}{\tau}}).$$

The thermal time constant τ is determined from measurement as exponential fit parameter.

Figure 11:
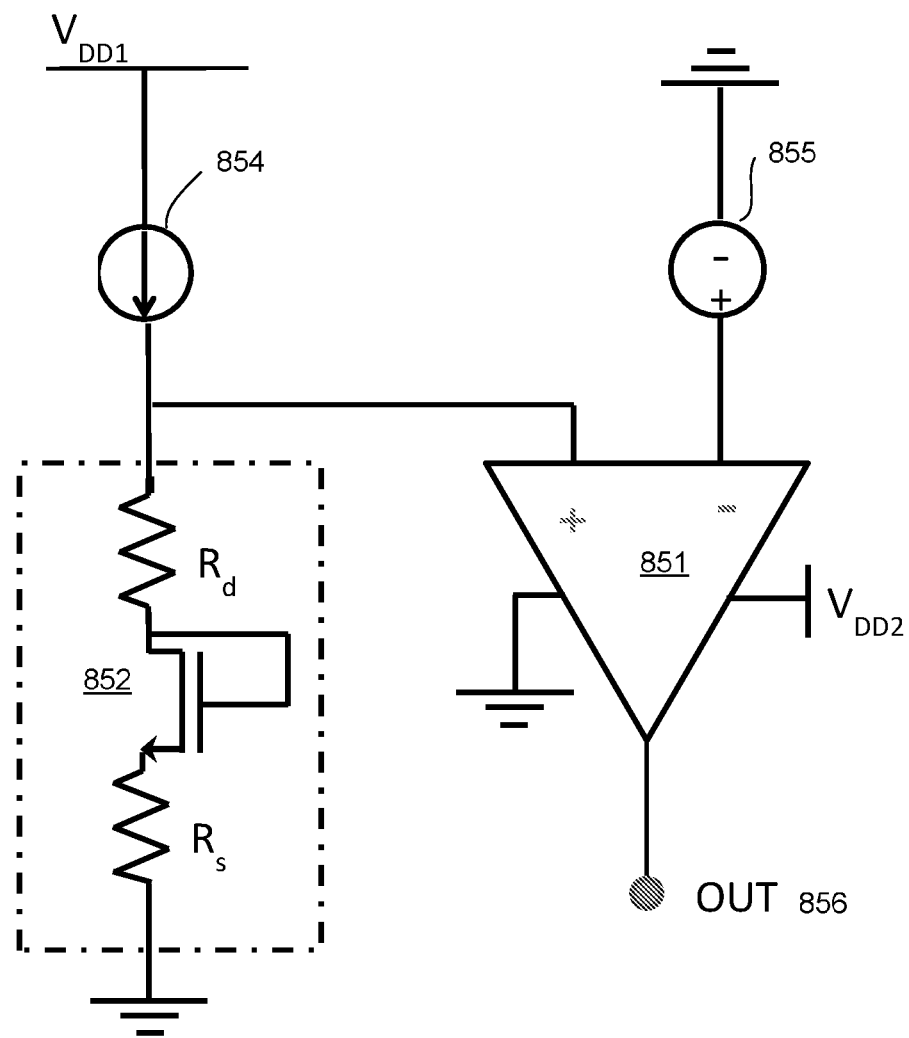
FIG. 11 illustrates a test circuit according to an embodiment of the invention.

FIG. 11 (should be described before FIG. 12) illustrates a test circuit that applies direct differential measurements according to an embodiment of the invention.

The test circuit included a current source 854 for providing current pulses that are synchronized with voltage pulses (virtual reference) provided by voltage source 855.

The voltage drop over a pressure level sensor 852 is fed to a non-inverting input of differential amplifier 851 and the inverting input of the differential amplifier is fed by voltage source 855.

The output 856 of the differential amplifier 856 outputs a signal that represents the heating of the pressure sensing element 852.

The current pulses were rectangular pulses of current with length 100 ms and duty-cycle 50% (period 200 msec).

The current of each current pulse was changed from zero to amplitude value in time about 50 μsec.

The virtual reference were rectangular pulses of voltage with the same parameters (length 100 ms and duty-cycle 50%) were used. For balancing the differential amplifier the voltage amplitude was equaled the value of voltage dropped on pixels.

In this arrangement the pressure sensing element was a transistor that was connected as a diode and W/L=2.5/40=1/16.

The measurement results are illustrated in FIGS. 13-18.

Figure 12:
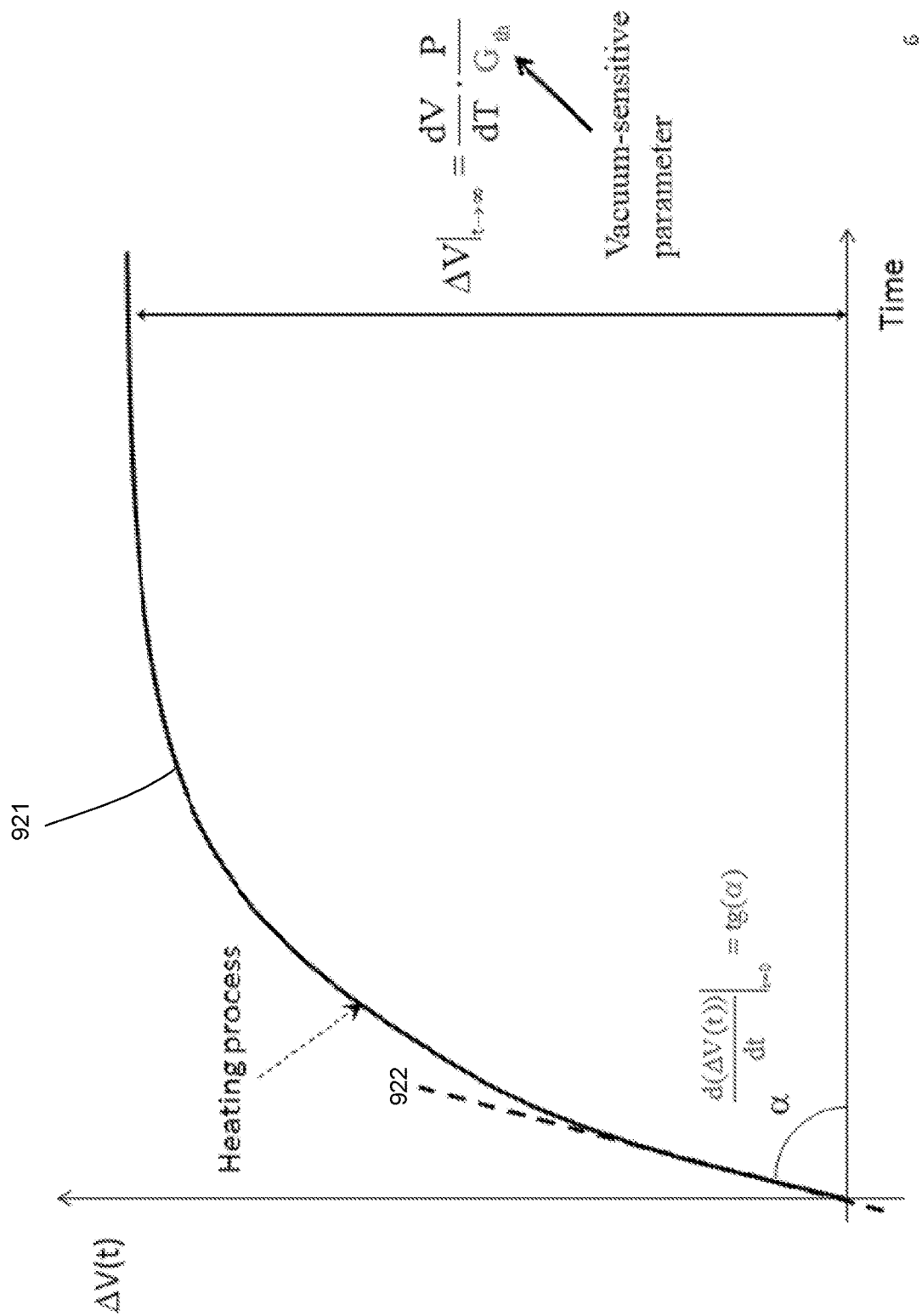
FIG. 12 illustrates the relationship between the heating process of a pressure sensing element and various thermal parameters.

FIG. 12 illustrates the relationship between the heating process of a pressure sensing element and various thermal parameters.

The heating process is represented curve 921 that illustrates the change of voltage across the pressure sensing element over time.

The initial slope 922 of curve 921 (the slope at the beginning of the heating process—substantially at a beginning of a current pulse) is denoted dV/Dt. The heating process is an exponential process with a thermal time constant.

At the end of the heating process the voltage drop stabilizes to a steady state value denoted ΔV 923.

The steady state value equals the initial slope (dV/dT) multiplied by the heat power (P) and divided by the pressure sensitive value of G (also denoted $G_{th}$).

Curve 921 illustrates the heating process related to a single input signal pulse.

Figure 13:
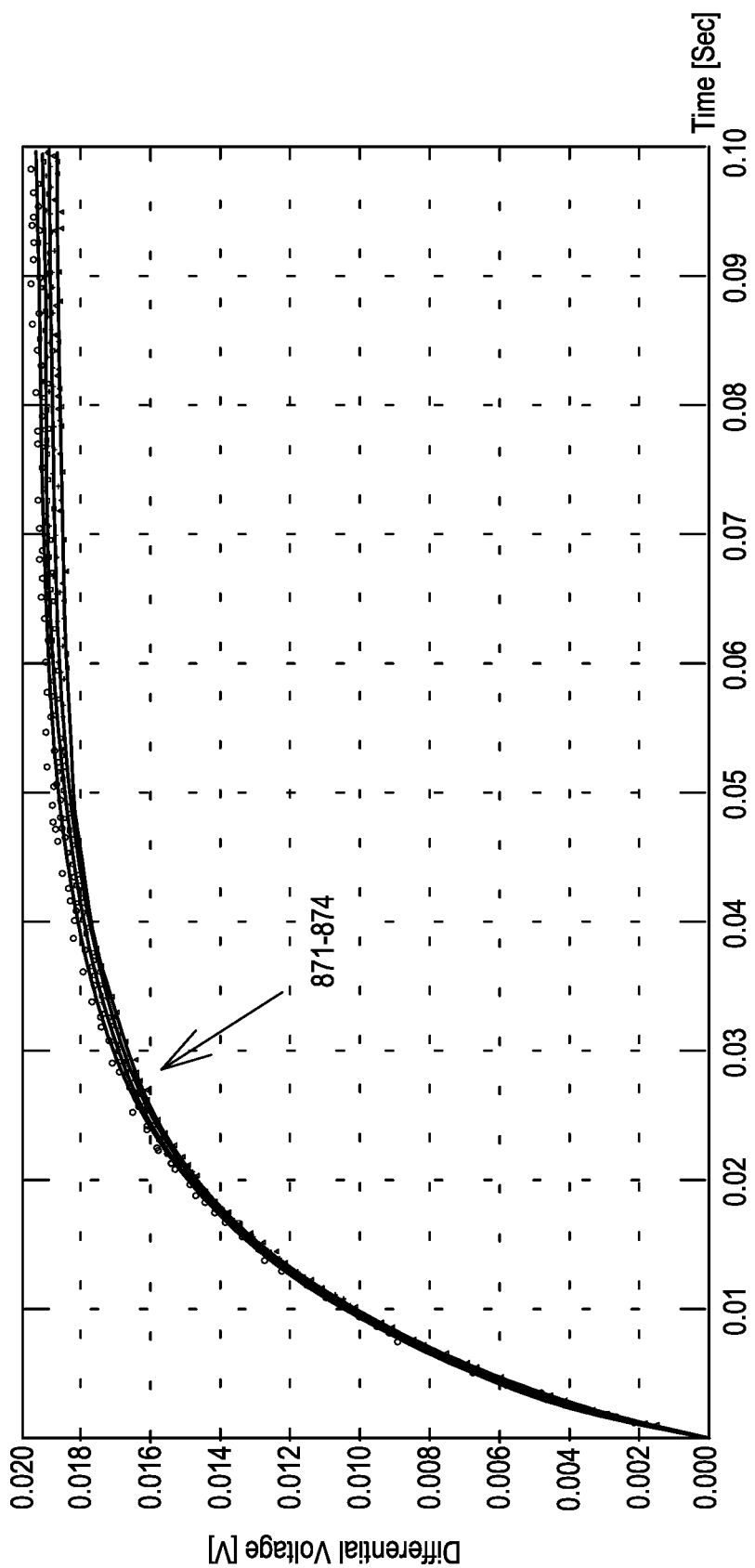
FIG. 13-18 illustrate tests according to an embodiment of the invention.

FIG. 13 shows (curves 871-874) time dependence of differential voltage from WLP measured in saturation at current ≅1.5 mA (V≅1 V).

Figure 14:
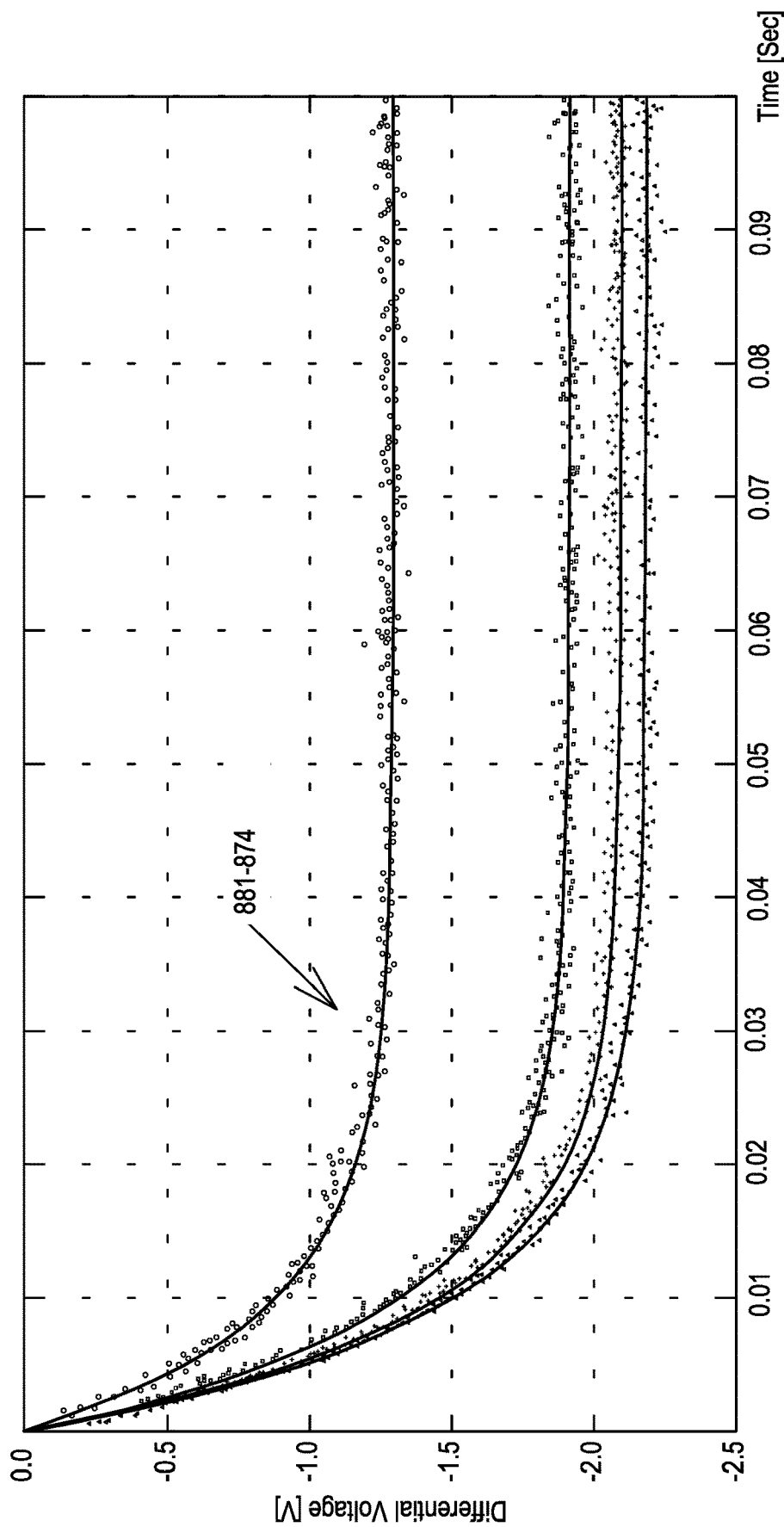
Figure 15:
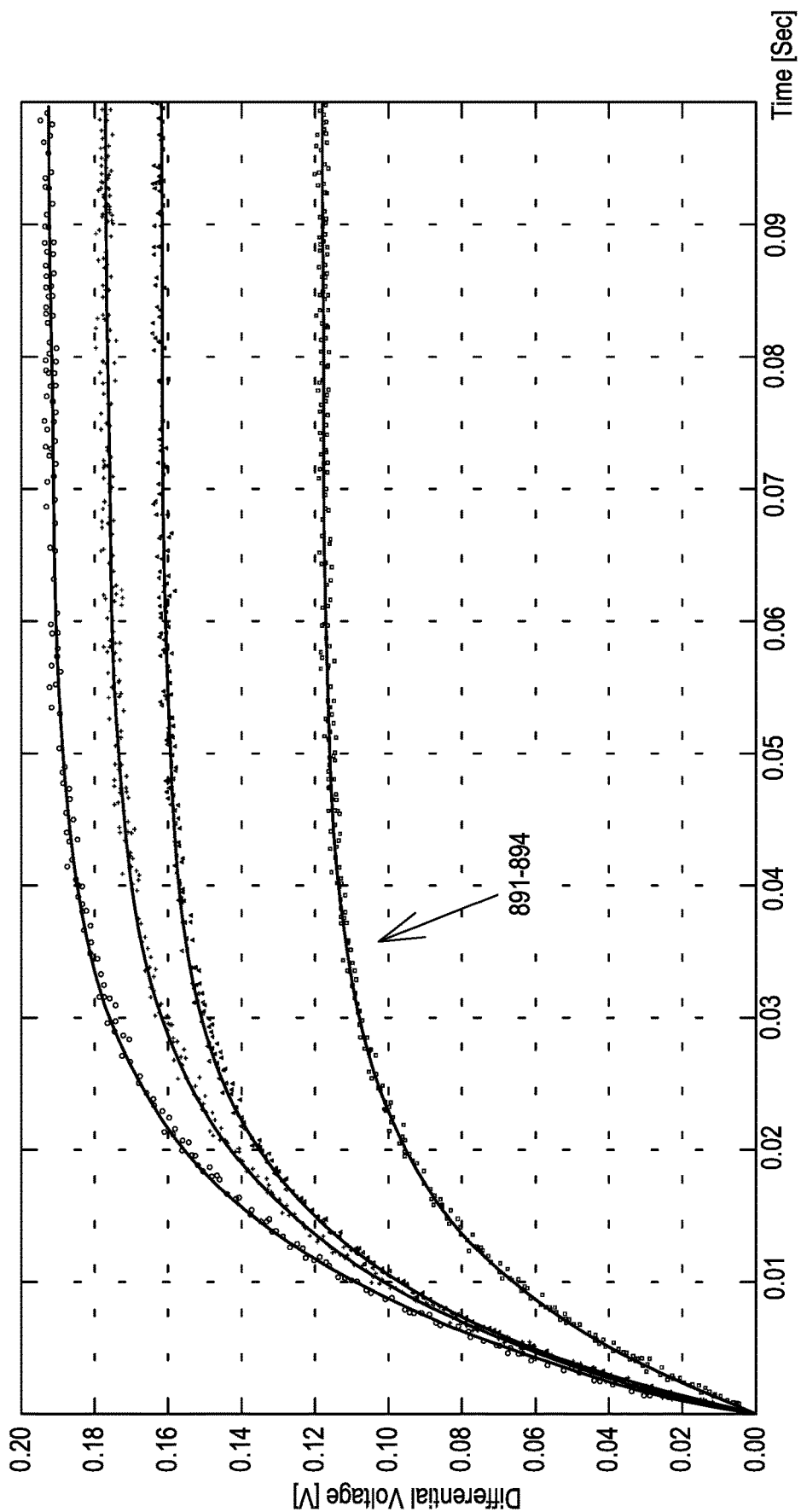

FIGS. 14 and 15 show (curves 881-884 and 891-894 respectively) time dependencies of differential voltage for Pixels D5 from WLP in two operation points: sub-threshold ≅1 mA; ≅360 mV (FIG. 14) and saturation ≅43 mA; ≅1V (FIG. 15). According exponential fit time constant was determined as 8.5 msec and 11.8 msec.

Figure 16:
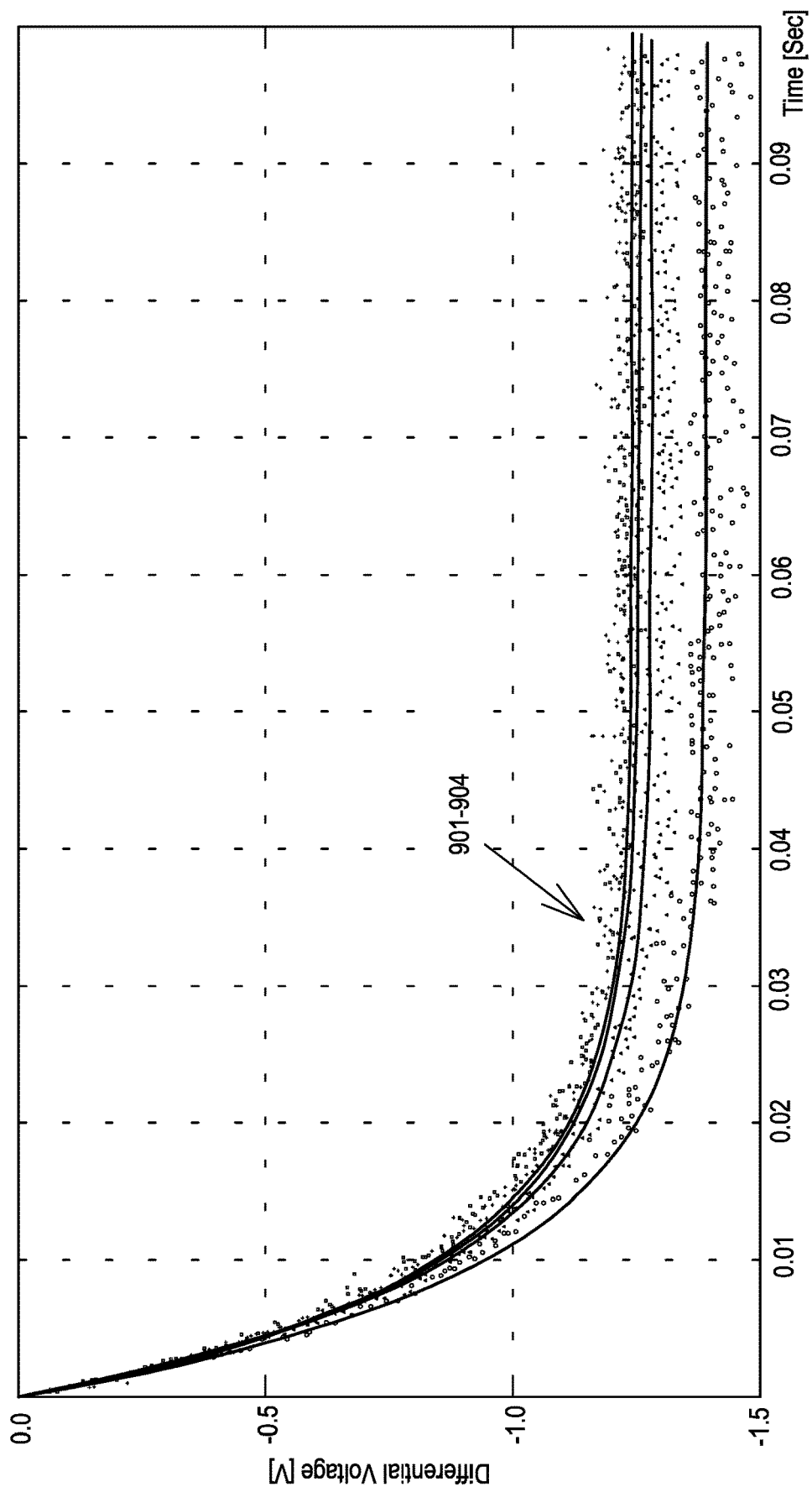
Figure 17:
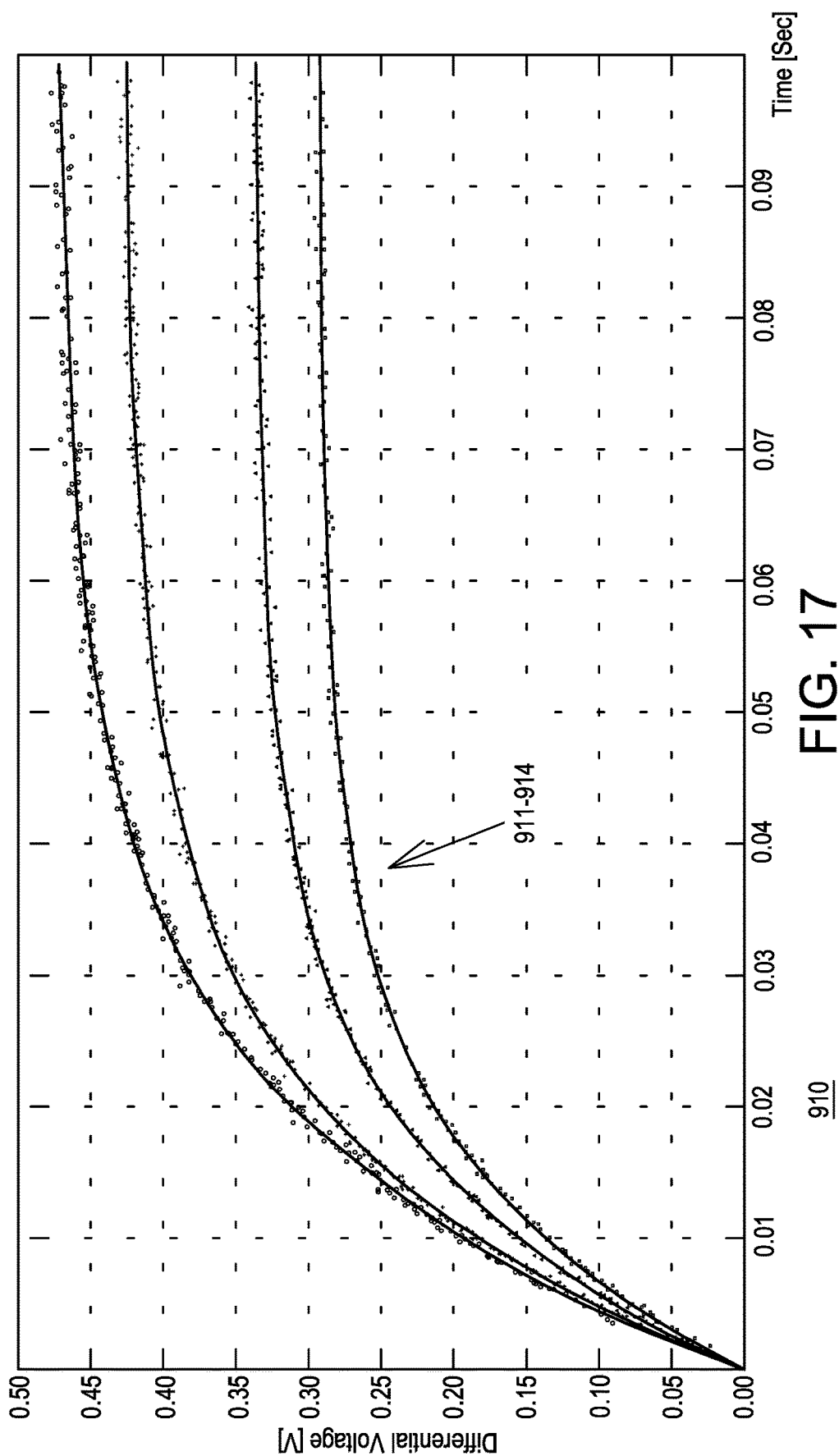

FIGS. 16 and 17 show (curves 901-904 and 911-914 respectively) time dependencies of differential voltage for Pixels D5 from in two operation points: sub-threshold ≅1 mA; ≅360 mV (FIG. 16) and saturation ≅43 mA; ≅1V (FIG. 17). According exponential fit time constant was determined as 8.85 msec and 17 msec.

Figure 18:
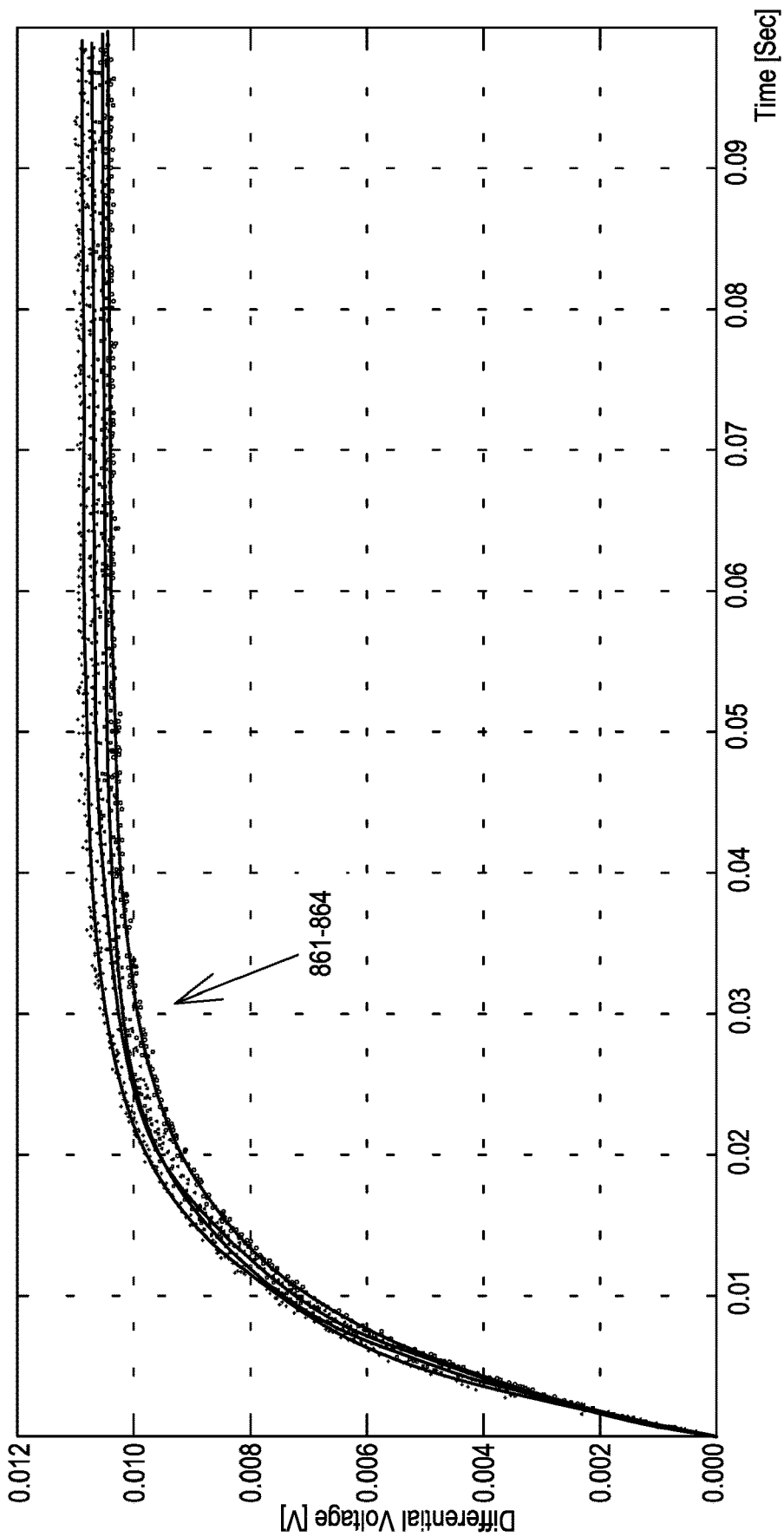

FIG. 18 shows (curves 861-864) time dependencies of differential voltage for pixels measured in saturation at current ≅1.5 mA (V≅1V). According exponential fit time constant was determined as ≅13.5 msec.

Figure 19:
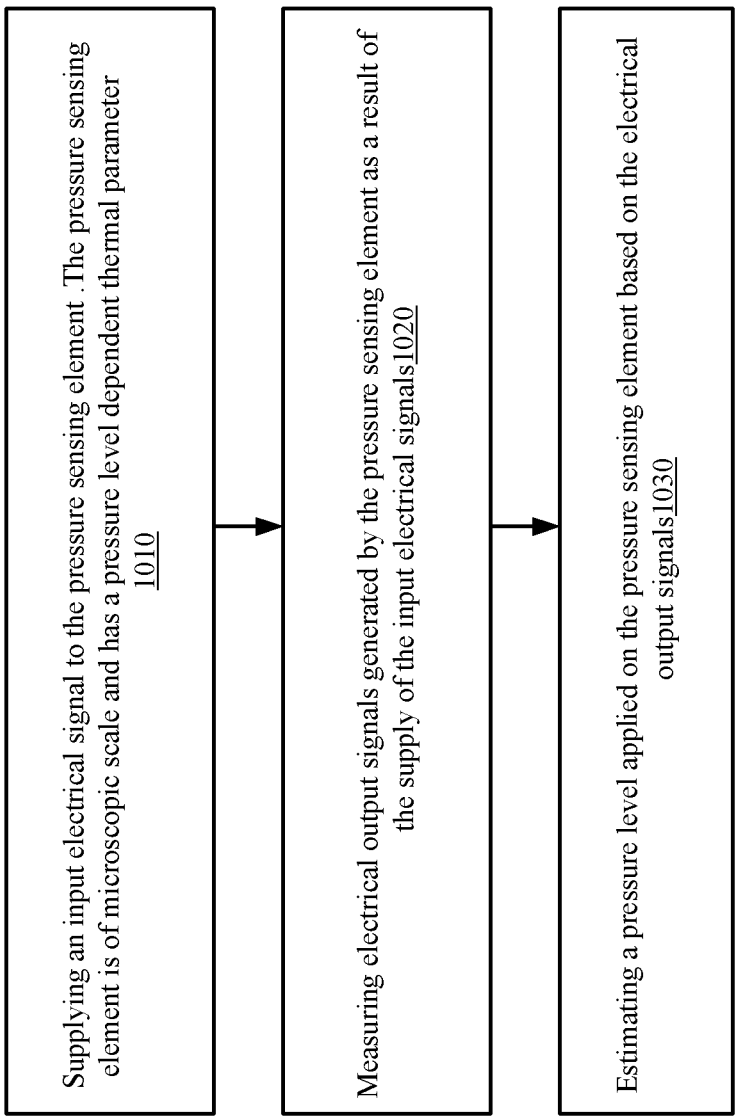
FIG. 19 illustrates a method according to an embodiment of the invention.

FIG. 19 illustrates method 1000 according to an embodiment of the invention.

Method 1000 is for sensing a pressure level applied on a pressure sensing element.

Method 1000 may start by step 1010 of supplying an input electrical signal to the pressure sensing element. The pressure sensing element is of microscopic scale and has a pressure level dependent thermal parameter. The input electrical signal may be a current pulse, a voltage pulse or any other signal.

Step 1010 is followed by step 1020 of measuring electrical output signals generated by the pressure sensing element as a result of the supply of the input electrical signals. The electrical output signals may be measured during different points of time.

Step 1020 may be followed by step 1030 of estimating a pressure level applied on the pressure sensing element based on the electrical output signals.

There may be provided a mapping (equation, lookup table) between the temperature of the gas reactive element (or the levels of the electrical output signals) and the pressure level sensed by the pressure sensing element. The mapping may be used for determining the pressure level based on the temperature (or the electrical output signals).

Method 1000 may be executed by any circuits, device and/or apparatus illustrated in the specification.

For example the pressure sensing element may be positioned within a chamber and wherein the pressure level applied on the pressure sensing element is a pressure level within the chamber.

The pressure sensing element may be used only for pressure sensing.

Alternatively, the pressure sensing element may be used for operations that differ from pressure sensing. For example—sensing radiation.

The pressure level dependent parameter may be a thermal time constant of the pressure sensing element.

The pressure level dependent parameter may be an initial slope (or any other slope) of the change of voltage developed over the pressure sensing element over time and a steady state voltage developed on the pressure sensing element.

Step 1030 may include estimating the thermal time constant of the pressure sensing element based on a steady state electrical output signal and based on an initial rate of change of the electrical output signals.

The input electrical signals may be spaced apart pulses.

The pressure sensing element may be a Microelectromechanical Systems (MEMS) element or a Nanoelectromechanical Systems (NEMS) element.

The pressure sensing element may be a suspended transistor that is thermally isolated from a bulk of the pressure sensing device.

The pressure sensing device may be manufactured by wafer level packaging technology In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Although specific conductivity types or polarity of potentials have been described in the examples, it will be appreciated that conductivity types and polarities of potentials may be reversed.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements.

The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A pressure sensing device comprising:
   a pressure sensing element that is of microscopic scale and has a pressure level dependent thermal parameter; wherein the pressure level dependent parameter is a thermal time constant of the pressure sensing element;
   a signal source that is configured to supply an input electrical signal to the pressure sensing element; and
   a monitor that is configured to (a) measure electrical output signals generated by the pressure sensing element as a result of the supply of the input electrical signal and (b) estimate a pressure level applied on the pressure sensing element based on the electrical output signals by estimating the thermal time constant of the pressure sensing element based on a steady state electrical output signal and based on an initial rate of change of the electrical output signals.

2. The pressure sensing device according to claim 1 wherein the pressure sensing element is positioned within a chamber and wherein the pressure level applied on the pressure sensing element is a pressure level within the chamber.

3. The pressure sensing device according to claim 1 wherein the pressure sensing element is used solely for sensing pressure.

4. The pressure sensing device according to claim 1 wherein the pressure sensing element is not solely dedicated for sensing pressure.

5. The pressure sensing device according to claim 1 wherein the input electrical signal comprises spaced apart pulses.

6. The pressure sensing device according to claim 1 wherein the pressure sensing element is a Microelectromechanical Systems (MEMS) element or a Nanoelectromechanical Systems (NEMS) element.

7. The pressure sensing device according to claim 1, wherein the pressure sensing element is a suspended transistor that is thermally isolated from a bulk of the pressure sensing device.

8. The pressure sensing device according to claim 1 wherein the pressure sensing device is manufactured by wafer level packaging technology.

9. A method for sensing a pressure level applied on a pressure sensing element, the method comprising:
   supplying an input electrical signal to the pressure sensing element; wherein the pressure sensing element is of microscopic scale and has a pressure level dependent thermal parameter; wherein the pressure level dependent parameter is a thermal time constant of the pressure sensing element;
   measuring electrical output signals generated by the pressure sensing element as a result of the supply of the input electrical signal; and
   estimating a pressure level applied on the pressure sensing element based on the electrical output signals by estimating the thermal time constant of the pressure sensing element based on a steady state electrical output signal and based on an initial rate of change of the electrical output signals.

10. The method according to claim 9 wherein the pressure sensing element is positioned within a chamber and wherein the pressure level applied on the pressure sensing element is a pressure level within the chamber.

11. The method according to according to claim 9 comprising utilizing the pressure sensing element only for sensing pressure.

12. The method according to claim 9 comprising utilizing the pressure sensing element for operations that differ from sensing pressure.

13. The method according to claim 9 wherein the input electrical signal comprises spaced apart pulses.

14. The method according to claim 9 wherein the pressure sensing element is a Microelectromechanical Systems (MEMS) element or a Nanoelectromechanical Systems (NEMS) element.

15. The method according to claim 9, wherein the pressure sensing element is a suspended transistor that is thermally isolated from a bulk of the pressure sensing device.

16. The method according to claim 9 wherein the pressure sensing device is manufactured by wafer level packaging technology.

17. A semiconductor device that comprises an enclosure and a semiconductor apparatus that is enclosed in the enclosure; wherein the semiconductor apparatus comprises:

a pressure sensing element that is of microscopic scale and has a pressure level dependent thermal parameter;

a signal source that is configured to supply, at different points in time, input electrical signals to the pressure sensing element; and a monitor that is configured to (a) measure electrical output signals generated by the pressure sensing element as a result of the supply of the input electrical signals and (b) estimate a pressure level applied within the enclosure based on the electrical output signals;

wherein the pressure level dependent parameter is a thermal time constant of the pressure sensing element;

and the monitor is configured to estimate the thermal time constant of the pressure sensing element based on a steady state electrical output signal and based on an initial rate of change of the electrical output signals.

18. The semiconductor device according to claim 17 wherein the semiconductor apparatus is a semiconductor die.

19. The semiconductor device according to claim 17 wherein the semiconductor apparatus is manufactured by wafer level packaging.

\* \* \* \* \*